United States Patent
Weil et al.

(10) Patent No.: US 6,615,429 B2
(45) Date of Patent: Sep. 9, 2003

(54) APPARATUS FOR POSITIONING A PATIENT-SUPPORT DECK

(75) Inventors: Paul R. Weil, Lawrenceburg, IN (US); Mark A. Graham, Batesville, IN (US); Christian H. Reinke, Wilmington, OH (US)

(73) Assignee: Hill-Rom Services, Inc., Wilmington, DE (US)

( * ) Notice: Subject to any disclaimer, the term of this patent is extended or adjusted under 35 U.S.C. 154(b) by 0 days.

(21) Appl. No.: 09/874,710

(22) Filed: Jun. 5, 2001

(65) Prior Publication Data

US 2002/0029419 A1 Mar. 14, 2002

Related U.S. Application Data

(63) Continuation-in-part of application No. 09/365,334, filed on Jul. 30, 1999, now Pat. No. 6,240,582.

(51) Int. Cl.[7] ............................................. A61G 13/08
(52) U.S. Cl. ........................ 5/601; 5/614; 378/209
(58) Field of Search ........................... 5/601, 613, 614; 378/177, 209; 108/143

(56) References Cited

U.S. PATENT DOCUMENTS

| | | | |
|---|---|---|---|
| 2,605,151 A | | 7/1952 | Shampaine |
| 3,281,141 A | | 10/1966 | Smiley et al. |
| 3,588,500 A | | 6/1971 | Koerner |
| 3,757,129 A | | 9/1973 | Hogan |
| 3,845,947 A | | 11/1974 | Lee |
| 3,868,103 A | * | 2/1975 | Pageot et al. ............... 137/596 |
| 3,980,288 A | * | 9/1976 | Mitchell et al. ............... 5/601 |
| 4,013,019 A | | 3/1977 | Horsey |
| 4,061,324 A | | 12/1977 | Kvaerna et al. |
| 4,195,829 A | | 4/1980 | Reser |
| 4,326,613 A | | 4/1982 | Houlberg |
| 4,327,596 A | | 5/1982 | Simon |
| 4,700,938 A | | 10/1987 | Chambron |
| 4,769,584 A | | 9/1988 | Irigoyen et al. |
| 4,773,637 A | | 9/1988 | Jarin |
| 4,956,592 A | | 9/1990 | Schulte et al. |
| 4,984,774 A | * | 1/1991 | Zupancic et al. ........... 254/122 |
| 4,989,848 A | | 2/1991 | Monroe |
| 5,181,288 A | | 1/1993 | Heaton et al. |
| 5,220,698 A | | 6/1993 | Hannant |
| 5,441,129 A | | 8/1995 | Porter et al. |
| 5,469,588 A | | 11/1995 | DiMatteo et al. |
| 5,490,297 A | | 2/1996 | Bradcovich et al. |
| 5,659,909 A | * | 8/1997 | Pfeuffer et al. ................ 5/600 |
| 6,038,718 A | | 3/2000 | Pennington et al. |
| 6,202,230 B1 | | 3/2001 | Borders |
| 6,226,821 B1 | | 5/2001 | Heimbrock et al. |
| 6,240,582 B1 | * | 6/2001 | Reinke ........................ 378/209 |

FOREIGN PATENT DOCUMENTS

| | | |
|---|---|---|
| EP | 0 522 730 | 1/1993 |
| EP | 0 650 696 | 5/1995 |
| EP | 0 923 922 | 6/1999 |
| WO | WO 01/08621 | 2/2001 |

* cited by examiner

*Primary Examiner*—Michael F. Trettel
(74) *Attorney, Agent, or Firm*—Bose McKinney & Evans LLP

(57) ABSTRACT

A patient-support apparatus includes a base, a patient-support deck, a deck-positioning assembly coupling the patient-support deck to the base, and a locking mechanism, the locking mechanism having a first state to prevent longitudinal movement of the patient-support deck relative to the base, and a second state to allow longitudinal movement of the patient-support deck relative to the base.

40 Claims, 13 Drawing Sheets

APPARATUS FOR POSITIONING A PATIENT-SUPPORT DECK

This application is a continuation-in-part of U.S. patent application Ser. No. 09/365,334, filed Jul. 30, 1999, which issued as U.S. Pat. No. 6,240,582 on Jun. 5, 2001, the disclosure of which is incorporated herein by reference.

BACKGROUND AND SUMMARY OF THE INVENTION

The present invention relates to an apparatus for positioning a patient-support deck and particularly, to an apparatus that moves a patient-support deck longitudinally relative to a base of a patient-support device. More particularly, the present invention relates to an apparatus for longitudinally moving a patient-support deck to facilitate taking x-ray or fluoroscopic images of a patient resting on a mattress supported by the patient-support deck.

Many conventional patient-support devices, such as operating tables and imaging tables, have mechanisms that are used to move a patient-support deck of the device longitudinally relative to a base of the device. Such adjustments in the longitudinal position of the patient-support deck may be made so that x-rays or fluoroscopic images can be taken of a patient supported by the patient-support deck. Some X-ray devices and other types of imaging devices have C-arms that are movable to positions having portions of the C-arm above and below the patient-support deck. Thus, it is desirable for patient-support devices to have a minimum amount of structure in the area beneath the patient-support deck to minimize the interference of the structure with the C-arm.

In accordance with one embodiment of the present invention, a patient-support apparatus includes a base, a patient-support deck that has a longitudinal length and a transverse width, and a deck-positioning assembly coupling the patient-support deck to the base. The patient-support deck is supported with respect to the deck-positioning assembly for longitudinal movement. Additionally, the deck-positioning assembly includes an actuator having a first portion and a second portion that moves transversely relative to the first portion. Furthermore, the deck-positioning assembly includes a transmission assembly configured to convert transverse movement of the second portion relative to the first portion into longitudinal movement of the patient-support deck relative to the base.

In preferred embodiments, the actuator is a linear actuator, such as a hydraulic cylinder, and the second portion moves axially along a first transverse axis relative to the first portion. Also in preferred embodiments, the transmission assembly includes a threaded shaft and a ball nut coupled to the threaded shaft. The threaded shaft is rotatable about a second transverse axis and the linear actuator is coupled to the ball nut so that extension and retraction of the second portion of the linear actuator relative to the first portion moves the ball nut along the threaded shaft which causes the threaded shaft to rotate. Also in preferred embodiments, the transmission assembly includes a pinion coupled to the threaded shaft and a rack coupled to the patient-support deck. The pinion engages the rack such that rotation of the threaded shaft and pinion causes longitudinal movement of the rack and patient-support deck relative to the base.

In accordance with another embodiment of the present invention, a patient-support apparatus includes a base, a patient-support deck having a longitudinal length and a transverse width, and a deck-positioning assembly coupling the patient-support deck to the base. The patient-support deck is supported with respect to the deck-positioning assembly for longitudinal movement. The deck-positioning assembly includes a shaft rotatable about a transverse axis between a first position and a second position. A rack is coupled to the patient-support deck and a lock assembly is coupled to the shaft. The lock assembly includes a member that moves in response to rotation of the shaft. The member engages the rack when the shaft is in the first position to prevent longitudinal movement of the patient-support deck relative to the base. The member is disengaged from the rack when the shaft is in the second position to allow longitudinal movement of the patient-support deck relative to the base.

In preferred embodiments, an actuator, such as an electric solenoid, is provided for moving the shaft between the first and second positions. Also in preferred embodiments, the member of the lock assembly is a pawl. One preferred lock assembly includes a cam coupled to the shaft and engaging the pawl so that rotation of the shaft rotates the cam to move the pawl into and out of engagement with the rack. After the lock assembly is unlocked, the patient-support deck is manually movable relative to the base. Also in preferred embodiments, an angle sensor is coupled to the deck positioning assembly. If the angle sensor indicates that the patient-support deck is in a non-horizontal position, then the actuator is disabled preventing the lock assembly from being unlocked.

In accordance with another embodiment of the present invention, a patient-support apparatus includes a base, a patient-support deck having a longitudinal length and a transverse width, and a deck-positioning assembly coupling the patient-support deck to the base. The patient-support deck is supported with respect to the deck-positioning assembly for longitudinal movement. The deck-positioning assembly includes a rod attached to the patient-support deck. A lock assembly is attached to the rod and includes a member that engages the rod in a first state to prevent longitudinal movement of the patient-support deck relative to the base, and disengages the rod in a second state to allow longitudinal movement of the patient-support deck relative to the base. An actuator coupled to the member selects the first and second states of the member. Also in preferred embodiments, an angle sensor is coupled to the deck positioning assembly. If the angle sensor indicates that the patient-support deck is in a tilted position, then the actuator is disabled from selecting the second state, thus preventing the lock assembly from being unlocked.

Additional features of the invention will become apparent to those skilled in the art upon consideration of the following detailed description of the preferred embodiment exemplifying the best mode of carrying out the invention as presently perceived.

BRIEF DESCRIPTION OF THE DRAWINGS

The detailed description particularly refers to the accompanying figures in which.

DETAILED DESCRIPTION OF THE DRAWINGS

Figure 1:
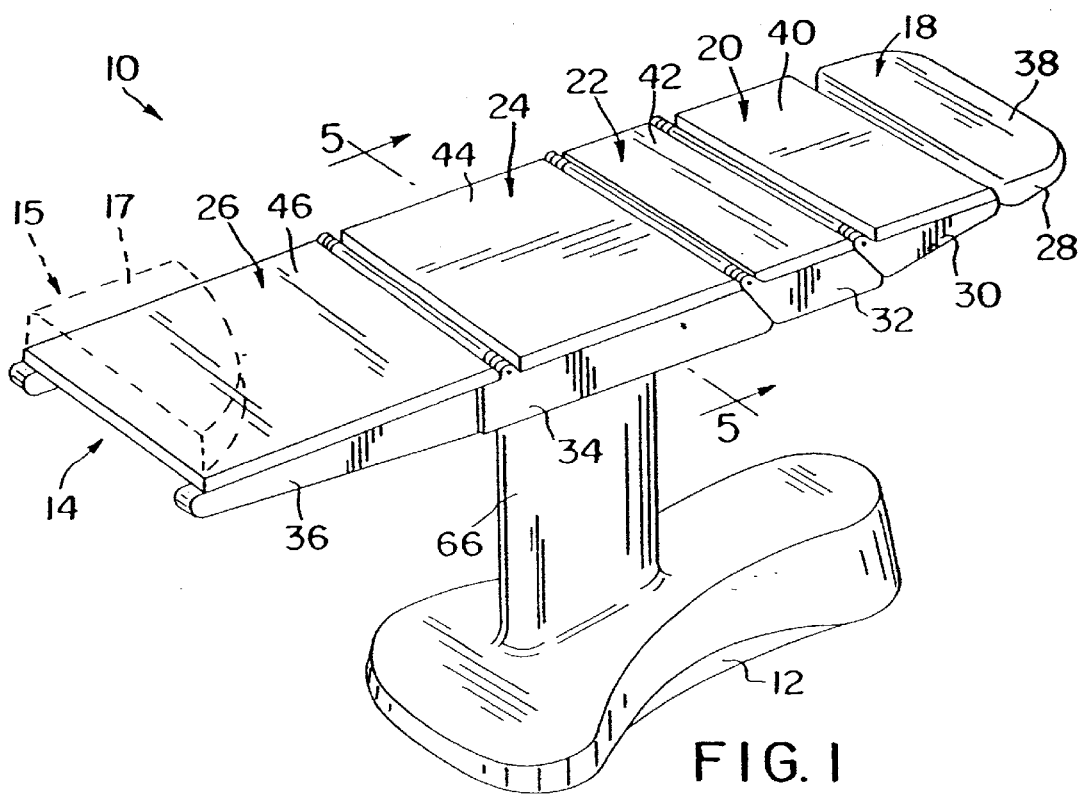
FIG. 1 is a perspective view of a patient-support apparatus in accordance with the present invention showing a patient-support deck having a plurality of articulated deck sections arranged in coplanar relation, a base beneath the patient-support deck, and a cosmetic cover overlying the base and shrouding a deck-positioning assembly which couples the patient-support deck to the base.
Figure 2:
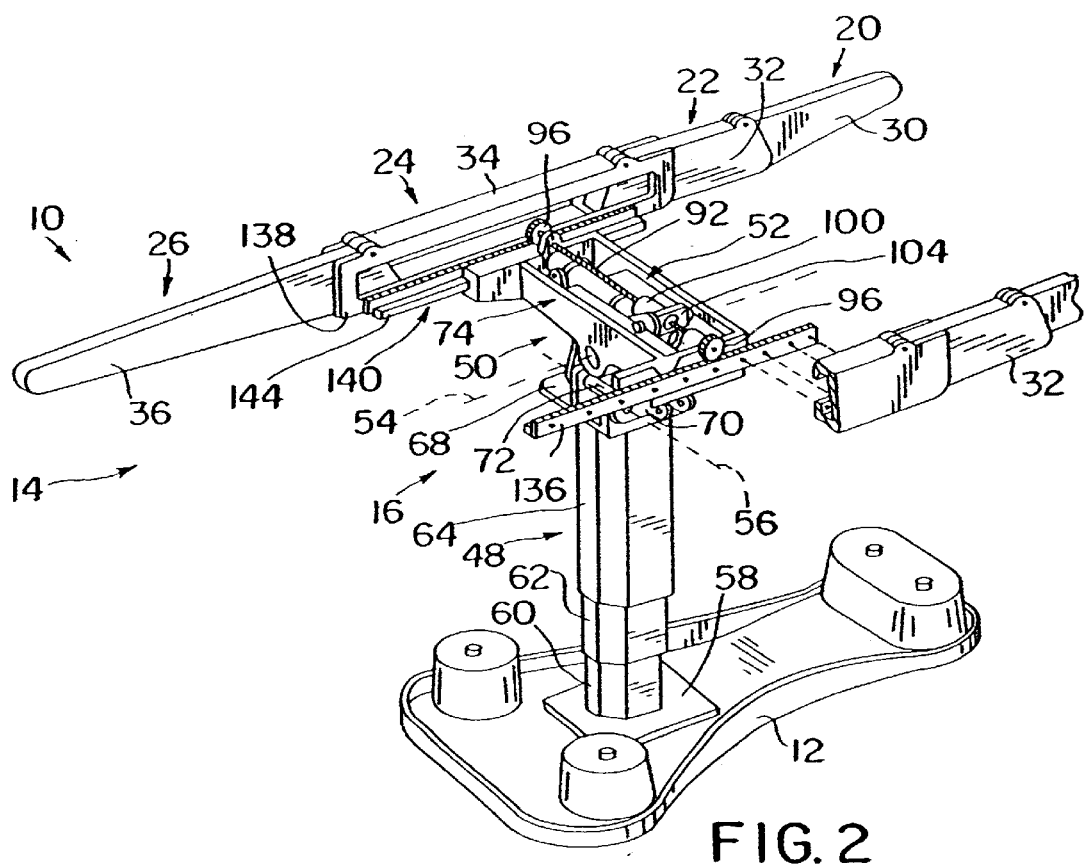
FIG. 2 is a perspective view of the patient-support apparatus of FIG. 1, with portions broken away, showing the deck-positioning assembly including a hi/lo mechanism extending vertically upwardly from the base, a tilt/trend mechanism situated atop the hi/lo mechanism, and a deck-slide mechanism coupling the tilt/trend mechanism to the patient-support deck.

A patient-support apparatus 10, such as an operating table or an imaging table, includes a base 12 and a patient-support deck 14 supported relative to base 12 as shown in FIG. 1. A mattress 15, a portion of which is shown in FIG. 1 (in phantom), includes an upwardly facing patient-support surface 17 and is supported by deck 14. A deck-positioning assembly 16 is coupled to base 12 and is coupled to deck 14 as shown in FIG. 2. Deck-positioning assembly 16 includes a hi/lo mechanism 48, a tilt/trend mechanism 50, and a deck-slide mechanism 52 as shown in FIG. 2. The present invention relates to features of deck-slide mechanism 52 as discussed below in further detail.

Patient-support deck 14, in the illustrated embodiment, is articulated and has a head section 18, an upper back section 20, a lower back section 22, a seat section 24, and a foot section 26. Sections 18, 20, 22, 24, 26 are serially hinged together for pivoting movement about respective transverse axes. Although illustrative deck 14 includes five deck sections 18, 20, 22, 24, 26, it is within the scope of the invention as presently perceived for deck 14 to have a different number of deck sections and to have deck sections that pivot about axes having orientations other than transverse. An example of an alternative patient-support deck is shown and described in U.S. patent application Ser. No. 09/187,990 which is assigned to the assignee of the present invention and which is hereby incorporated herein by reference.

Deck sections 18, 20, 22, 24, 26 each include frame members 28, 30, 32, 34, 36, respectively, and panels 38, 40, 42, 44, 46, respectively, that are coupled to associated frame members 28, 30, 32, 34, 36. One or more of panels 28, 30,

32, 34, 36 are made from a radiotransluscent material that permits x-rays and rays from fluoroscopic imaging machines to pass therethrough. Deck 14 further includes drive mechanisms (not shown) that operate to articulate sections 18, 20, 22, 26 relative to seat section 24 and relative to base 12.

Illustrative hi/lo mechanism 48 operates to raise and lower deck 14 relative to base 12. Tilt/trend mechanism 50 is situated atop hi/lo mechanism 18 and operates to tilt deck 14 side to side about a longitudinal axis 54 and to tilt deck 14 front to rear about a transverse axis 56. Deck-slide mechanism 54 is coupled to tilt/trend mechanism 50 and operates to move deck 14 longitudinally relative to base 12. Thus, articulation of deck sections 18, 20, 22, 26 of patient-support deck 14 and operation of mechanisms 48, 50, 52 of deck-positioning assembly 16 permits patient-support apparatus 10 to be moved into a multitude of configurations for supporting a patient thereon.

Illustrative hi/lo mechanism 48 includes a bottom plate 58 coupled to base 12 and telescoping first, second, and third support tubes 60, 62, 64 situated above plate 58. Mechanism 48 further includes a drive mechanism (not shown) positioned within the interior regions of tubes 60, 62, 64. This drive mechanism operates to extend and retract tubes 60, 62, 64 thereby raising and lowering, respectively, deck 14 relative to base 12. Patient-support apparatus 10 includes a cover 66 that shrouds base 12 and hi/lo mechanism 48. Cover 66 includes telescoping portions (not shown) that extend and retract as tubes 60, 62, 64 extend and retract.

Illustrative tilt/trend mechanism 50 includes a first member 68 coupled to the top end of tube 64. Mechanism 50 further includes a second member 70 coupled to first member 68 for pivoting movement about transverse axis 56. Mechanism 50 includes suitable couplers, such as pivot pin 72 shown in FIG. 2, for coupling members 68, 70 together. Mechanism 50 includes a third member or platform 74 that is coupled to second member 70 for pivoting movement about longitudinal axis 54. Suitable couplers (not shown) are provided for coupling platform 74 and second member 70 together. Mechanism 50 also includes drive mechanisms (not shown) that operate to pivot second member 70 about transverse axis 56 relative to first member 68 and that operate to pivot platform 74 about longitudinal axis 54 relative to second member 70.

It will be appreciated that various mechanical and electromechanical actuators and drivers may be used to raise and lower deck 14 relative to base 12, to tilt deck 14 relative to base 12, and to articulate deck sections 18, 20, 22, 24, 26. It is well known in the art that electric, hydraulic, and pneumatic actuators in combination with various types of transmission elements including lead screw drives and various types of mechanical linkages may be used to create relative movement of portions of patient-support devices. As a result, the term "drive mechanism(s)" is intended to cover all types of mechanical, electromechanical, hydraulic, and pneumatic mechanisms, including manual cranking mechanisms of all types, and including combinations thereof such as hydraulic cylinders in combination with electromechanical pumps for pressuring fluid received by the hydraulic cylinders.

Figure 3:
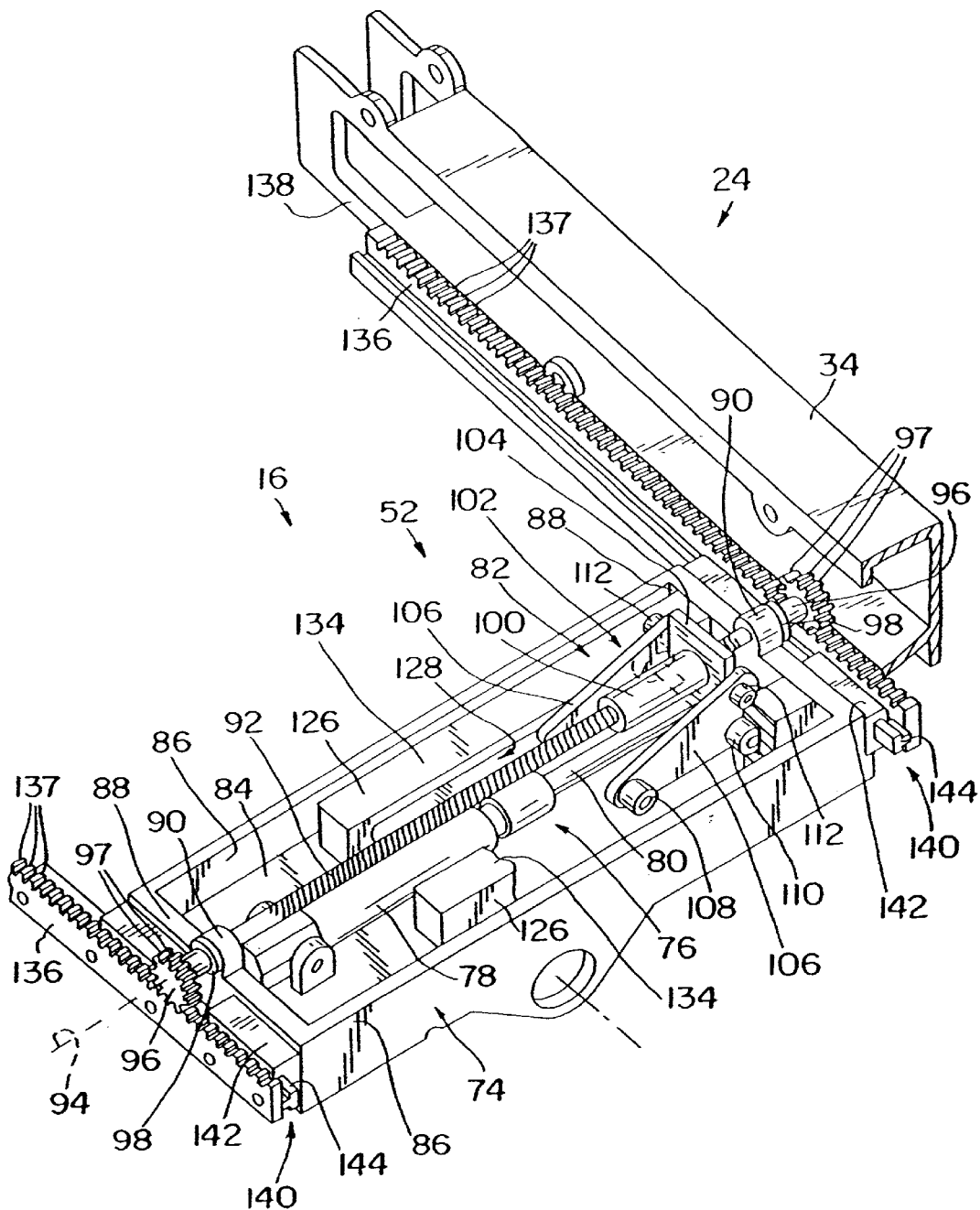
FIG. 3 is an enlarged perspective view of a portion of the patient-support apparatus of FIG. 2, with portions broken away showing a transversely oriented hydraulic cylinder coupled to an upper platform of the tilt/trend mechanism, a threaded shaft supported for rotation about a transverse axis relative to the upper platform, a ball nut coupled to the threaded shaft, a carriage assembly coupling the hydraulic cylinder to the ball nut, a pair of pinions coupled to ends of the threaded shaft, a pair of racks coupled to the seat section of the patient-support deck, and a pair of linear bearings supporting the racks and patient-support deck relative to the upper platform.

Deck-slide mechanism 52 includes an actuator 76, shown for example in FIG. 3, having a first portion 78 and a second portion 80 that moves transversely relative to first portion 78. Mechanism 52 further includes a transmission assembly 82 that converts transverse movement of second portion 80 into longitudinal movement of deck 14. In preferred embodiments, actuator 76 is a hydraulic cylinder (hereinafter referred to as hydraulic cylinder 76) having a housing (hereinafter referred to as housing 78) and a piston rod (hereinafter referred to as piston rod 80). However, it is within the scope of the invention as presently perceived for other types of actuators, such as a pneumatic cylinder or a linear actuator having a lead screw drive driven by an electric motor, to be provided in deck-slide mechanism 52 in lieu of hydraulic cylinder 76.

Platform 74 includes a bottom wall 84, a pair of transversely extending side walls 86 extending upwardly from bottom wall 84, and a pair of longitudinally extending end walls 88 extending upwardly from bottom wall 84 as shown in FIG. 3. Side walls 86 cooperate with end walls 88 to define a compartment above bottom wall 84. A pair of flanges 84 extend upwardly from bottom wall 84 and housing 78 of hydraulic cylinder 76 is coupled to flanges 84 as shown in FIG. 3. Hydraulic cylinder 76 is positioned to lie within the compartment defined by walls 84, 86, 88. Hydraulic fluid is pumped into or extracted from housing 78 in a conventional manner to extend and retract piston rod 80 along a transverse axis 89.

Platform 74 includes a pair of shaft-support flanges 90, each of which extend upwardly from a respective end wall 88 as shown in FIG. 3. Transmission assembly 82 includes a threaded shaft 92 that is supported by flanges 90 for rotation about a transverse axis 94. In preferred embodiments, hydraulic cylinder 76 and shaft 92 are coupled to platform 74 such that axis 94 is parallel with and vertically above axis 89. Shaft 92 is positioned to lie above the compartment defined by walls 84, 86, 88 and end portions of shaft 92 extend outwardly beyond end walls 88 of platform 76. A pair of pinions 96 are coupled to respective end portions of shaft 92. Optionally, a pair of thrust washers or thrust bearings 98 may be provided between pinions 96 and flanges 90. In addition, a pair of radial bearings or bushings (not shown) may be provided to support shaft 92 relative to flanges 90. Of course, a pair of one-piece bushings, each having a thrust portion and a radial portion may also be used as an alternative.

Transmission assembly 82 includes a ball nut 100 coupled to shaft 92 for transverse axial movement along axis 94. Transmission assembly 82 further includes a carriage assembly 102 coupled to ball nut 100 and coupled to piston rod 80 as shown in FIGS. 3–6. Carriage assembly 102 includes a first plate 104 and a pair of second plates 106 that are coupled to first plate 102 as shown best in FIG. 4. Ball nut 100 is fixed to first plate 102. A first roller 108, a second roller 110, and a third or upper roller 112 are coupled to each of plates 106 by axle pins 114, 116, 118, respectively, for rotation about axes 120, 122, 124, respectively.

Illustratively, first rollers 108 are offset transversely from respective second rollers 110 and upper rollers 112 are positioned to lie vertically above respective second rollers 110 as shown in FIGS. 3–6. In addition, pivot axis 118 of rollers 112 intersects axis 94 of threaded shaft and pivot axes 120, 122 of associated rollers 108, 110 each intersect axis 89 of hydraulic cylinder 76 as shown best in FIG. 4. Thus, vertical distance 115 between axis 89 and axis 94 is substantially equivalent to vertical distance 117 between axis 122 and axis 124. Optionally, axle pins 118 may include portions which couple plates 106 to plate 104. In addition, axle pin 116 preferably is configured as a single axle pin such that rollers 110 are coupled to end portions thereof and such that piston rod 80 is coupled to a middle portion thereof.

Figure 4:
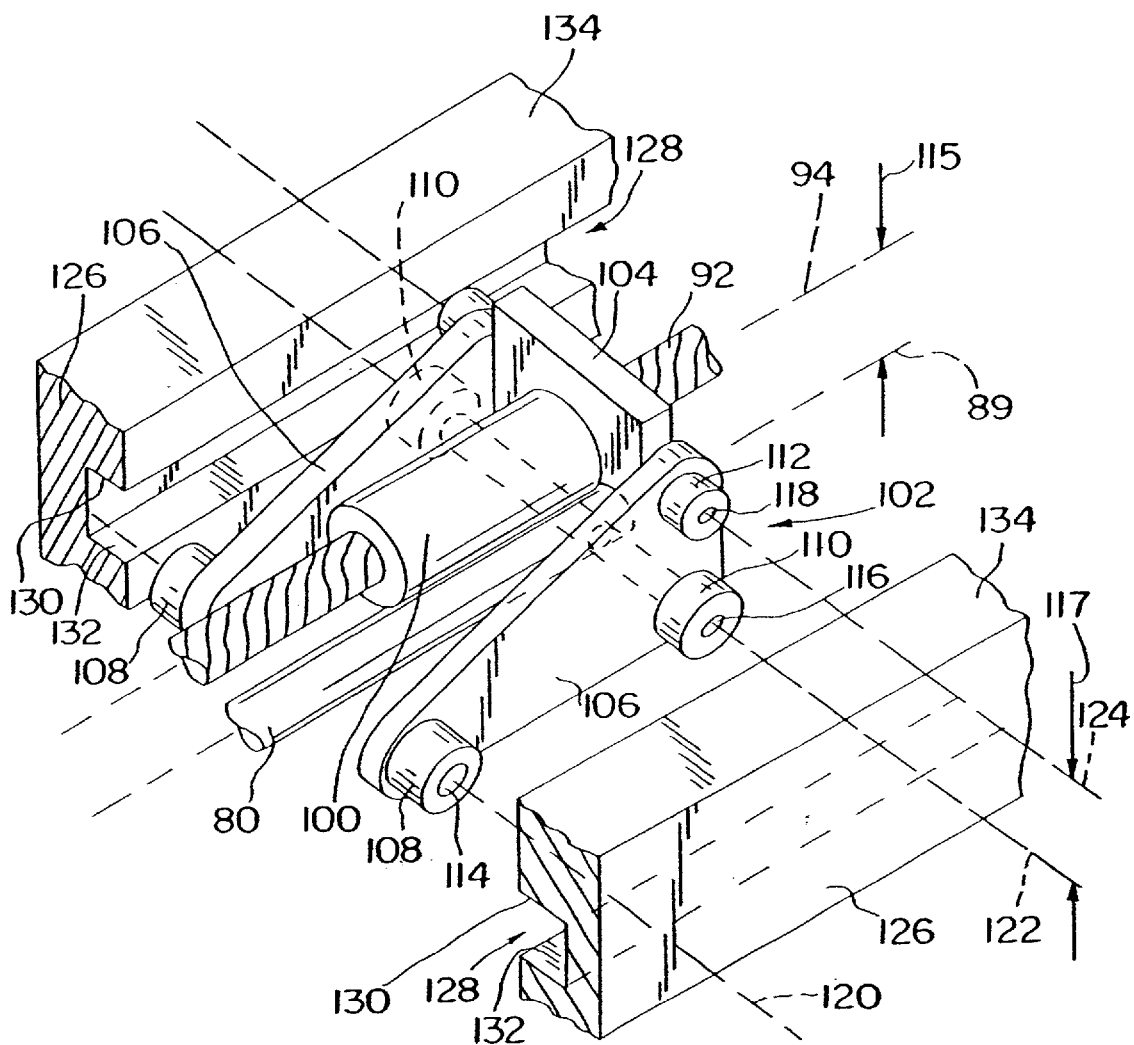
FIG. 4 is an exploded perspective view of the deck-slide mechanism, with portions broken away, showing details of the carriage assembly and showing portions of a pair of track members that guide the movement of the carriage assembly.

Transmission assembly 82 also includes a pair of track members 126, each of which is formed to include a slot or channel 128 as shown best in FIG. 4. Slot 128 defines a top track surface 130 and a bottom track surface 132. Rollers 108, 110 associated with each of plates 106 are received in slots 128 of respective track members 126. Each track member 126 includes an upper surface 134 upon which respective rollers 112 roll. The vertical spacing between track surfaces 130, 132 is only slightly larger than the diameter of rollers 108, 110 so that only a minimal amount of clearance exists between rollers 108, 110 and track surfaces 130, 132. Those skilled in the art will appreciate that each of rollers 108, 110 will engage only one of surfaces 130, 132 at any particular instance in time and that a small amount of clearance will exist between each of rollers 108, 110 and the other of surfaces 130, 132. Thus, track members 126 guide the movement of carriage assembly 102 during operation of deck-slide mechanism 52.

Figure 5:
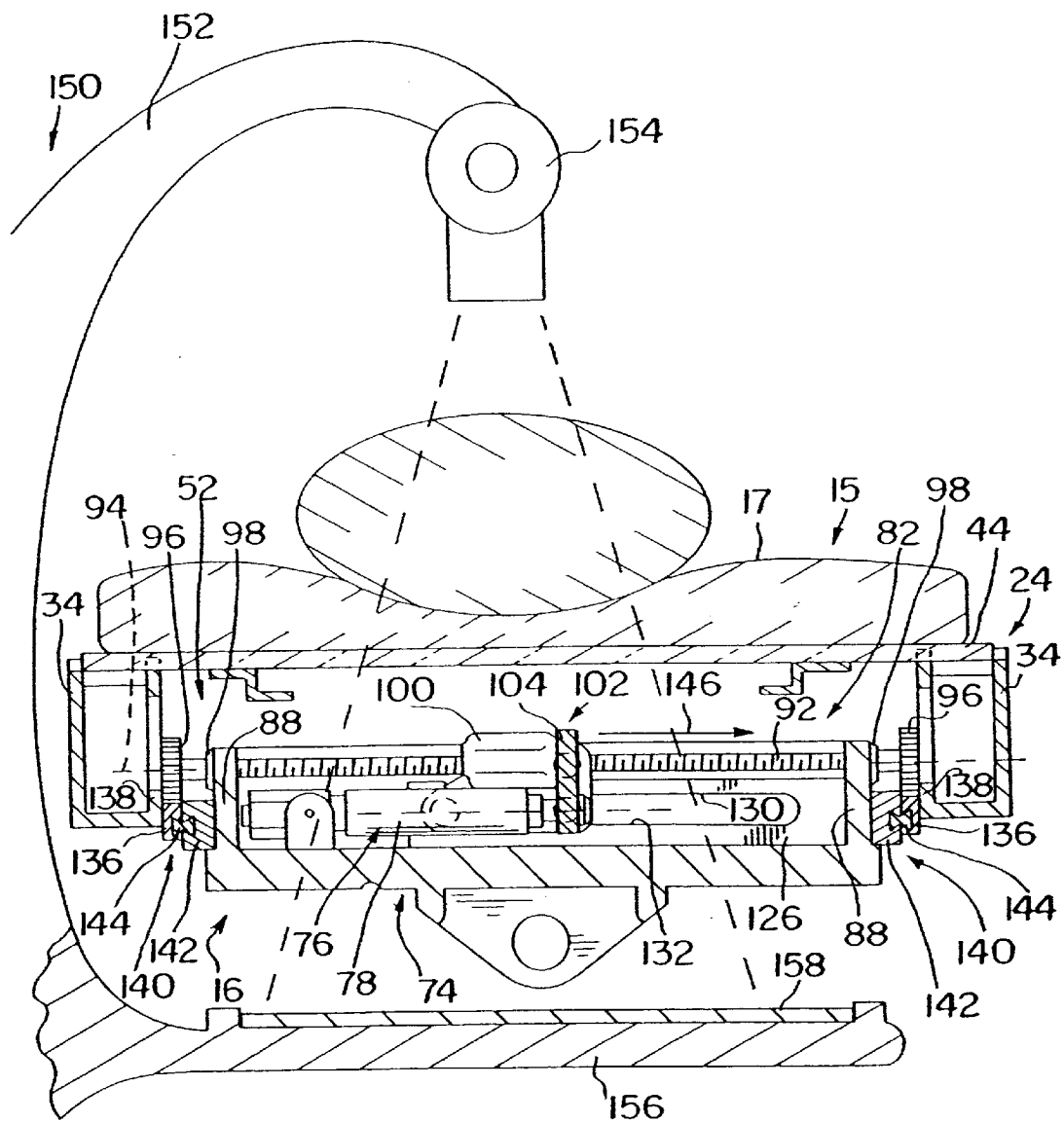
FIG. 5 is a sectional view taken along line 5—5 of FIG. 1 showing the piston rod of the hydraulic cylinder in a fully-retracted position having the ball nut positioned about half way between a right side and a left side of the patient-support deck and showing, diagrammatically, a C-arm imaging machine shooting an image of a patient supported by the patient-support deck.
Figure 6:
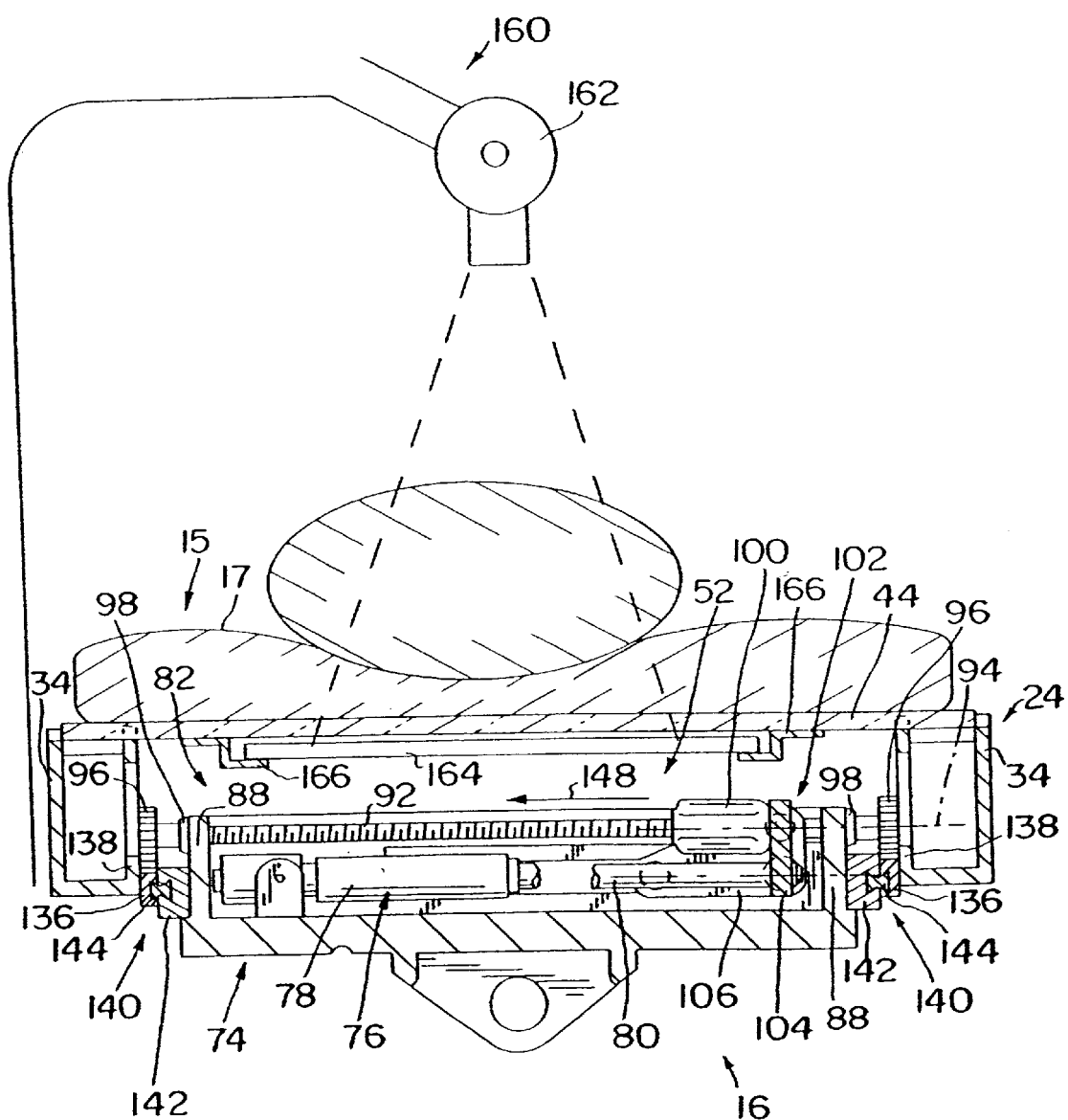
FIG. 6 is a sectional view similar to FIG. 5 showing the piston rod of the hydraulic cylinder in a fully-extended position having the ball nut positioned closer to the right side of the patient-support deck and showing, diagrammatically, an X-ray imaging machine shooting an image of a patient supported by the patient-support deck onto a cassette of film supported beneath a panel of the patient-support deck.

Transmission assembly 82 includes a pair of racks 136, each of which are coupled to respective vertical walls 138 of frame members 34 of seat section 24 as shown in FIGS. 3, 5 and 6. Pinions 96 each include a plurality of teeth 97 that engage associated teeth 137 of racks 136 in a conventional manner so that rotation of pinions 96 results in linear motion of racks 136. Deck-slide mechanism 52 includes a pair of linear bearings 140, each having a first member 142 coupled to platform 74 and a second member 144 coupled to a respective rack 136. Second member 144 slides relative to first member 142 when deck 14 moves longitudinally relative to base 12 and deck-positioning assembly 16. Thus, linear bearings 140 support deck 14 for longitudinal movement relative to deck-positioning assembly 16. Those skilled in the art will appreciate that other mechanisms, such as tracks and rollers or surface-to-surface contact between frame members 34 and platform 74, may be provided to support deck 14 for longitudinal movement relative to deck-positioning assembly 16. In addition, other options for the manner in which linear bearings 140 are coupled to platform 74 and to seat section 24 or racks 136 also will be readily apparent to those skilled in the art.

In use, hydraulic cylinder 76 is actuated either to extend or retract piston rod 80 relative to housing 78 thereby causing carriage assembly 102 either to move away from housing 78 in direction 146, shown in FIG. 5, or to move toward housing 78 in direction 148, shown in FIG. 6. As carriage assembly 102 moves, rollers 108, 110 roll within slot 128 relative to track members 126 and rollers 112 roll upon upper surfaces 134 of track members 126. Movement of carriage assembly 102 in directions 146, 148 causes ball nut 100 to move along axis 94 of shaft 92 in directions 146, 148, respectively. Because ball nut 100 is fixed to plate 104 of carriage assembly 102, ball nut 100 is constrained from rotating on shaft 92 and thus, movement of ball nut 100 along shaft 92 necessarily causes shaft 92 to rotate due to interaction between balls (not shown) of ball nut 100 and the threads of shaft 92. As shaft 92 rotates about transverse axis 94, pinions 96 also rotate about axis 94 causing longitudinal movement of racks 136 along with deck 14 which is coupled to racks 136.

When ball nut 100 moves in direction 146, shaft 92 and pinions 96 rotate in one direction and when ball nut 100 moves in direction 148, shaft 92 rotates in an opposite direction. Thus, the longitudinal direction of movement of deck 14 is dictated by the transverse direction of movement of ball nut 100. By having hydraulic cylinder 76, shaft 92, and track members 126 all transversely oriented, the longitudinal distance between side walls 86 of platform 74 can be kept to a minimum. In addition, the amount of longitudinal movement of deck 14 compared to the amount of transverse movement of ball nut 100 is dictated by the pitch of the threads of shaft 92 and the diameter of pinions 96. In a preferred embodiment of the present invention, five inches (12.7 cm) of transverse movement of ball nut 100 causes fourteen inches (35.6 cm) of longitudinal movement of deck 14. Thus, deck-slide mechanism 52 is packaged in a compact and efficient manner which provides imaging equipment with increased access for taking images of the portion of a patient supported on seat section 24.

It will be appreciated that it is within the scope of the present invention for mechanisms other than racks 136 and pinions 96 to be included in deck-slide mechanism 52 to convert rotation of shaft 92 into longitudinal movement of deck 14. For example, frictional contact between rollers mounted on shaft 92 and tracks mounted to seat section 24 could be employed in lieu of racks 136 and pinions 76. Those skilled in the art will also realize that sprockets mounted on shaft 92 and chains coupled to platform 74 and seat section 24 could be used as an alternative, as could pulleys mounted on shaft 92 and belts or cables coupled to platform 74 and seat section 24.

Figure 5A:
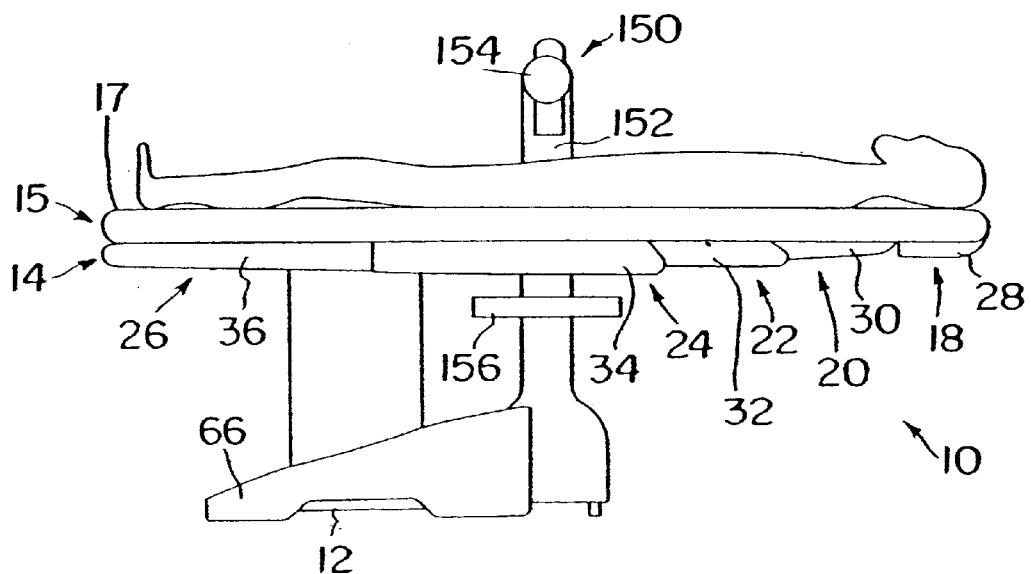
FIG. 5A is a side elevation view of the patient-support apparatus showing the patient-support deck moved to a forwardmost position relative to the base and showing the C-arm imaging machine shooting an image of the patient.
Figure 6A:
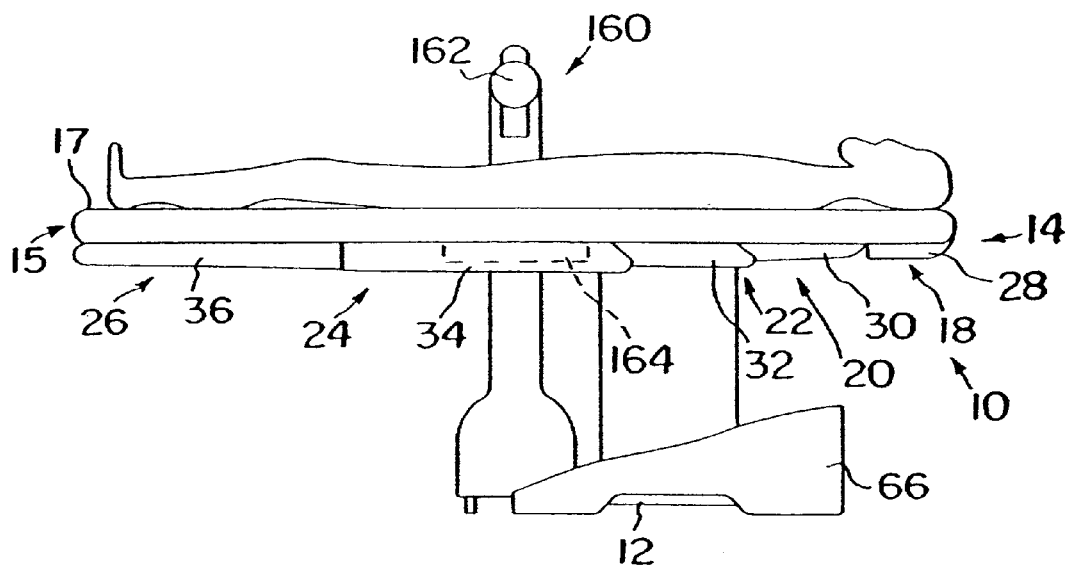
FIG. 6A is a side elevation view of the patient-support apparatus showing the patient-support deck moved to a rearwardmost position relative to the base and showing the X-ray imaging machine shooting an image of the patient.

FIGS. 5 and 5A show a fluoroscopic imaging machine 150 having a C-arm 152 with a beam generator 154 above deck 14 and a tray 156 beneath deck 14. Tray 146 supports a film cassette 158 that captures fluoroscopic images of the portion of the patient supported thereabove. FIGS. 6 and 6A show an X-ray imaging machine 160 having a beam generator 162 above deck 14. A film cassette 164 that captures X-ray images of the portion of the patient supported thereabove is supported beneath panel 44 of seat section 24 by a pair of brackets 166 as shown in FIG. 6. Deck 14 is shown in its forwardmost position in FIG. 5A and deck 14 is shown in its rearwardmost position in FIG. 6A. Thus, by using deck-slide mechanism 52 to move deck 14 between the forwardmost and rearwardmost positions, C-arm 152 is able to take images of portions of the patient that would otherwise be inaccessible. In addition, moving deck 14 to either the forwardmost position or the rearwardmost position makes it easier for a caregiver to load film cassette 164 into the proper position beneath panel 44.

Patient-support apparatus 10 may include a user input device (not shown) of any conventional type that is used to command the operation of the drive mechanisms (not shown) included in patient-support deck 14 and included in deck-positioning assembly 16 and that is also used to command the operation of actuator 76 of deck-slide mechanism 52. Examples of user input devices that may be included in patient-support apparatus 10 are shown and described in U.S. patent application Ser. No. 09/187,825 which is assigned to the assignee of the present invention and which is hereby incorporated by reference herein.

Those skilled in the art will appreciate that deck-slide mechanism 52 can be employed in any patient-support device in which longitudinal movement of a patient-support deck relative to a base is desired, whether or not the patient-support deck also raises, lowers, or tilts. Therefore, the term "deck-positioning assembly" as used in the claims is intended to cover all types of pedestal structures, frame assemblies, supports, and the like that may be used to couple a patient-support deck to a base.

A patient-support apparatus 210 includes a deck-positioning assembly 216 having an alternative embodiment deck-slide mechanism 252 as shown in FIGS. 7–10. Many components of patient-support apparatus 210 are substantially similar to like components of patient-support apparatus 10 and therefore, like reference numerals are used throughout to denote like components. Unlike deck-slide mechanism 52 which operates through actuator 76 and transmission assembly 82 to automatically move patient-support deck 14 longitudinally, deck-slide mechanism 252 operates to lock and unlock patient-support deck 14 for manual longitudinal sliding movement relative to base 12.

Figure 7:
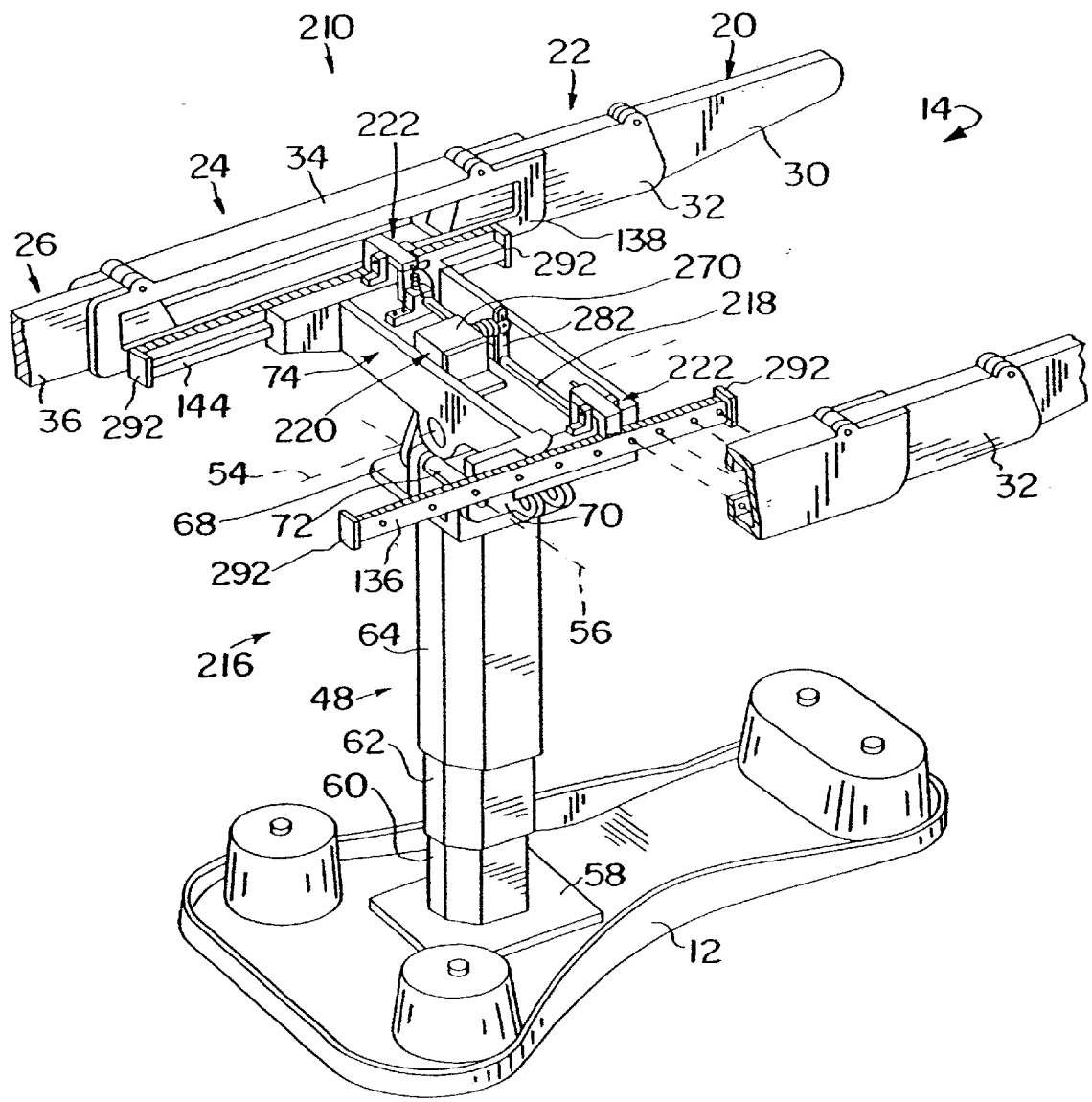
FIG. 7 is a perspective view, similar to FIG. 2, of an alternative embodiment patient-support apparatus in accordance with the present invention showing a base, a deck-positioning assembly including a hi/lo mechanism extending vertically upwardly from the base, a tilt/trend mechanism situated atop the hi/lo mechanism, and a deck-slide mechanism coupling the tilt/trend mechanism to the patient-support deck, the deck-slide mechanism including a lock assembly that operates to lock and unlock the patient-support deck for sliding movement relative to the base.
Figure 8:
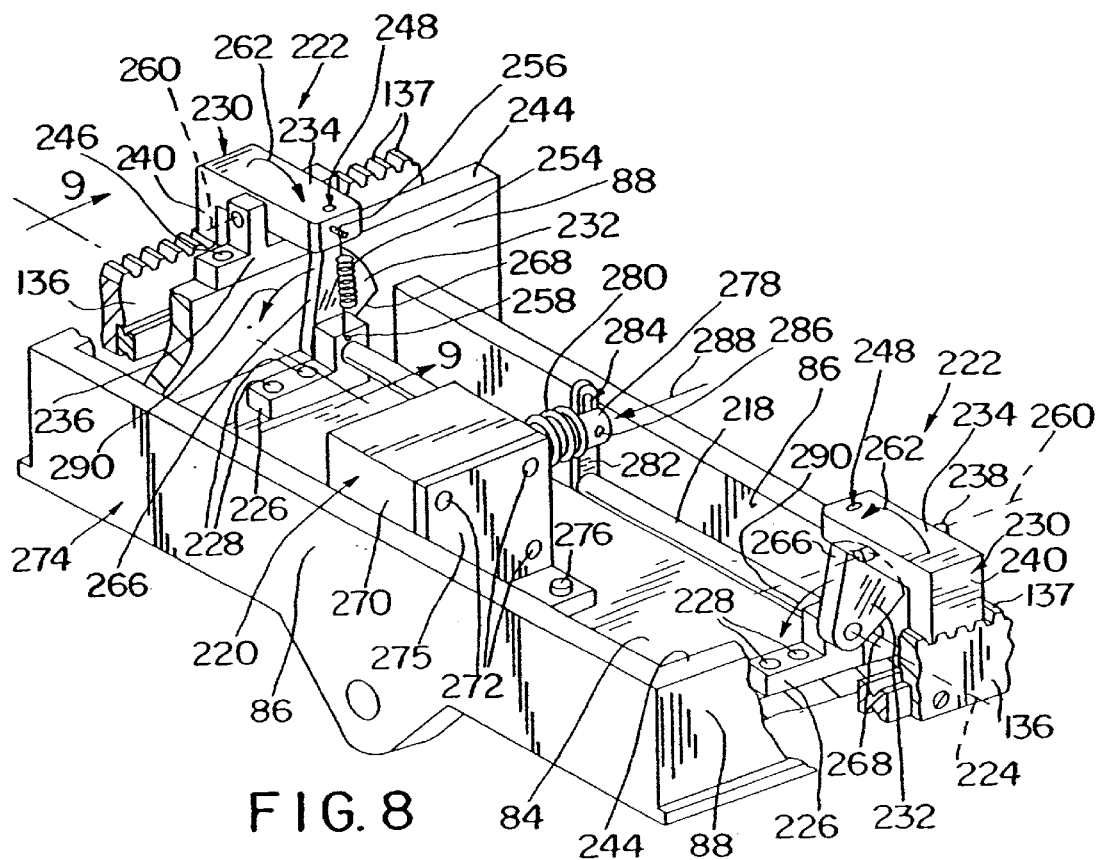
FIG. 8 is an enlarged perspective view of a portion of the patient-support apparatus of FIG. 7, with portions broken away, showing a shaft supported for rotation about a transverse axis relative to an upper platform of the tilt/trend mechanism, an actuator coupled to a link extending from the shaft, a pair of cams coupled to ends of the shaft, a pair of racks coupled to a seat section of the patient-support deck, a pair of linear bearings supporting the racks and patient-support deck relative to the upper platform, and a pair of pawls in a lock position engaging the respective racks to prevent longitudinal movement of the patient-support deck relative to the base.
Figure 9:
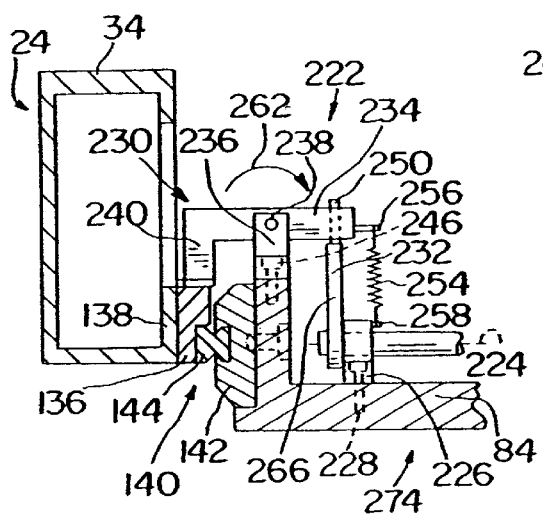
FIG. 9 is a sectional view taken along line 9—9 of FIG. 8 showing one of the pawls in the lock position.
Figure 10:
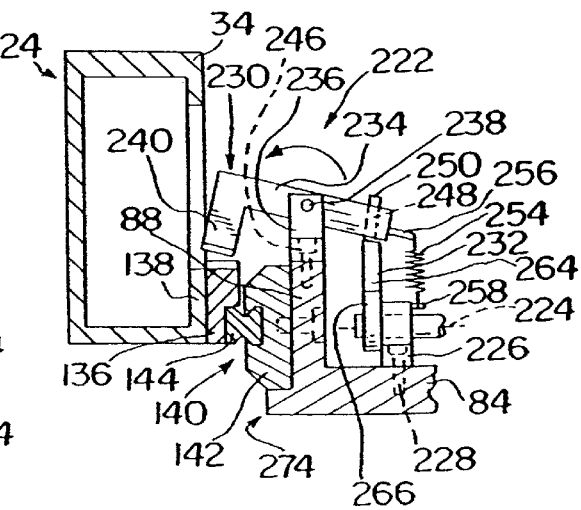
FIG. 10 is a sectional view, similar to FIG. 9, showing one of the pawls moved to an unlocking positioning disengaged from the respective rack to allow longitudinal movement of the patient-support deck relative to the base.

Deck-slide mechanism 252 includes a shaft 218, an actuator 220 that operates to rotate shaft 218 between first and second positions, and a pair of lock assemblies 222 coupled to shaft 218 as shown in FIG. 7. Shaft 218 is supported for rotation about a transverse axis 224 by a pair of brackets 226 that are coupled to bottom wall 84 of a platform 274 in any suitable manner such as by bolts 228 as shown in FIGS. 8–10. Each of the end portions of shaft 218 extend outwardly beyond respective brackets 226 but terminate between brackets 226 and the associated end walls 88 of platform 274. Illustratively, each bracket 226 is formed to include a bore that provides a plain bearing surface upon which shaft 218 rotates. Optionally, bearings or bushings (not shown) may be received within the bores of brackets 226 to support shaft 218 for rotation.

Lock assemblies 222 each include a member 230 that moves between a first or locking position, shown in FIGS. 7–9, and a second or unlocking position, shown in FIG. 10, in response to rotation of shaft 218 between its first and second positions. Each illustrated locking assembly 222 further includes a cam 232 coupled to the end portions of shaft 218 between the associated bracket 226 and wall 88 of platform 274. Cams 232 are fixed to shaft 218 to rotate therewith. In preferred embodiments, each member 230 is a pawl (hereinafter referred to as pawl 230) that is L-shaped having a first portion 234 coupled to a respective bracket 236 by a suitable coupler, such as a pin 238, and having a second portion 240 formed with one or more teeth 242 as shown best in FIG. 8. Brackets 236 are coupled to top surfaces 244 of end walls 88 in any suitable manner, such as by bolts 246. The first portion 234 of each pawl 230 is tapped with a threaded hole 248 and an adjuster or bolt 250 is threadedly received in hole 248. The lower end of each adjuster 250 is positioned to lie beneath first portion 234 of the respective cam 232 and is engaged by a cam surface 264 of the respective cam 232 as shown in FIGS. 9 and 10.

Lock assemblies 222 each include a spring 254 having an upper end coupled to first portion 234 of the respective pawl 230 in any suitable manner, such as by pin 256, and having a lower end coupled to the respective bracket 226 in any suitable manner, such as by pin 258. Pins 238 cooperate with brackets 236 to define respective longitudinal pivot axes 260 and springs 254 each act to bias pawls 230 to rotate about respective pivot axes 260 in the direction of arrows 262 shown in FIGS. 8 and 9. Of course, pawls 230 can only move in direction 262 when permitted to do so by movement of cams 232. Thus, springs 254 bias adjusters 250 into contact with cam surfaces 264 of respective cams 232. Cams 232 each include a long side 266 and a short side 268. Cam surfaces 264 smoothly arc between associated long sides 266 and short sides 268. As cams 232 rotate along with shaft 218 about axis 224, cam surfaces 264 wipe against the lower ends of adjusters 250 to change the position of pawls 230.

When pawls 230 are in the respective locking positions, adjusters 250 engage cam surfaces 264 closer to long sides 266 than short sides 268 of respective cams and teeth 242 engage teeth 137 of racks 136 thereby preventing racks 136 and patient-support deck 14 from moving longitudinally relative to base 12. Rotation of adjusters 250 fine tunes the position of pawls 230 relative to cams 232 to adjust the manner in which teeth 242 intermesh with teeth 137 when pawl 230 is in the locking position. When pawls 230 are in the respective unlocking positions, adjusters 250 engage cam surfaces 264 closer to short sides 268 than long sides 266 of respective cams 232 and teeth 242 are disengaged from teeth 137 of racks 136 which permits manual longitudinal movement of patient-support deck 14 relative to base 12.

Although illustrative lock assemblies 222 each include a pair of cams 232 that are coupled to shaft 218 and that move pawls 230 between the locking and unlocking positions, those skilled in the art will appreciate that mechanisms other than cams 232 can be employed in lock assemblies 222 without exceeding the scope of the present invention. For example, a pair of linkages coupling shaft 218 to respective pawls 218 could be included in lock assemblies 222 in lieu of cams 232. In addition, a cable or tether that is coupled to pawl 230 and that wraps around and unwraps from either shaft 218 or a pulley mounted on shaft 218 as shaft 218 rotates also would be within the scope of the present invention. Furthermore, sprockets mounted on shaft 218 could interact with chains coupled to respective pawls 230 to move pawls 230 between the locking and unlocking positions as shaft 218 rotates.

As previously described, deck-positioning assembly 216 includes an actuator 220 that operates to rotate shaft 218. Illustrated actuator 220 is an electric solenoid (hereinafter referred to as solenoid 220), although it is within the scope of the invention as presently perceived for any suitable device capable of causing rotation of shaft 218 to be included in deck-positioning assembly 216 in lieu of solenoid 220. Solenoid 220 includes a housing 270 that is coupled by suitable fasteners such as bolts 272 to a mounting bracket 275 which, in turn, is coupled by suitable fasteners such as bolts 276 to bottom wall 88 of platform 74 as shown in FIG. 8. Solenoid 220 also includes an output shaft 278 and a return spring 280 mounted on shaft 278. A portion of shaft 278 is situated inside housing 270 and a portion of shaft 278 is positioned to lie outside of housing 270.

A link 282 is fixed to a central portion of shaft 218 and extends perpendicularly therefrom as shown in FIG. 8. The distal end of link 282 is formed to include a slot 284. Output shaft 278 of solenoid 220 is coupled to link 282 by a pin 286, a middle portion of which is received in slot 284 and end portions of which are received in pin-receiving apertures formed in distal end portions of shaft 278 that lie on either side of link 282. When solenoid 220 is actuated in a conventional manner by applying an electric potential to leads (not shown) of solenoid 220, shaft 278 moves in the direction of arrow 288, shown in FIG. 8, such that shaft 278 retracts further into housing 270. Movement of shaft 278 in direction 288 causes link 282, shaft 218, and cams 232 to pivot about axis 224 in the direction of arrows 290, thereby permitting springs 254 to pivot pawls 230 about axes 260 in directions 262 from their respective locking positions to their respective unlocking positions.

When solenoid 220 is actuated moving shaft 278 in direction 288, pin 286 moves within slot 284 as link 282 rotates and, furthermore, link 282 compresses return spring 280 against housing 270. When solenoid 220 is deactuated by removing the electric potential from the leads thereof, spring 280 pushes against link 282 thereby rotating link 282, shaft 218, and cams 232 about axis 224 in a direction opposite to direction 288. Rotation of cams 232 about axis 224 in the direction opposite to direction 288 forces pawls 230 to move from the unlocking position, shown in FIG. 10, to the locking position, shown in FIG. 9. Additionally, rotation of link 282 in the direction opposite to direction 288 pulls pin 286 away from housing 270 of solenoid, thereby extending shaft 278 out of housing 270. Solenoid 220 is configured with conventional structure to limit the amount by which shaft 278 retracts into and extends out of housing 270. For example, complete compression of spring 280 or contact between shaft 278 and a first stop (not shown) inside housing 270 limits the retraction of shaft 278 into housing 270. In addition, contact between a shoulder (not shown) of shaft 278 and a second stop (not shown) inside housing 270 limits the extension of shaft 278 out of housing 270.

As previously described, when pawls 230 are moved to the respective unlocking positions, deck 14 is manually movable to change the longitudinal position of deck 14 relative to base 12. As deck 14 moves longitudinally, first members 142 of linear bearings 140 slide relative to second members 144. A set of stops or stop blocks 292, shown in FIG. 7, are provided for limiting the amount by which deck 14 may be longitudinally moved when pawls 230 are in the unlocking positions.

Figure 11:
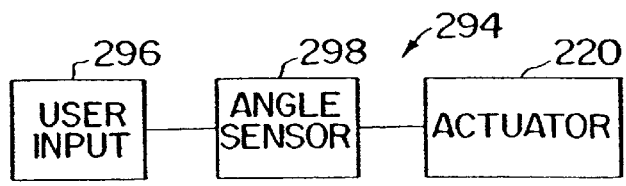
FIG. 11 is a block diagram of a portion of a control system for controlling the deck-positioning assembly of FIG. 7, showing a user input block, an angle sensor block, and an actuator block.

Patient-support apparatus 210 includes a control system that is used to command the operation of the various drive mechanisms (not shown) of deck-positioning assembly 216 and that is used to command the operation of actuator 220. An illustrative portion 294 of the control system associated with actuator 220 includes a user input 296 and an angle sensor 298 as shown diagrammatically in FIG. 11. User input 296 receives user input commands to lock and unlock each of lock assemblies 222 thereby controlling locking and unlocking of deck 14 relative to base 12. Angle sensor 298 is configured to sense whether seat section 24 is tilted about transverse axis 56. If seat section 24 is tilted in either direction about axis 56, then angle sensor 298 operates to disable actuator 220 from being actuated. If seat section 24 is in a horizontal position, as shown in FIG. 7, then angle sensor 298 operates to enable actuator 220 thereby permitting actuation of actuator 220. Disabling actuator 220 when seat section 24 is tilted about axis 56 enhances the safety of patient-support apparatus 210 because of the possibility that deck 14 would slide relative to platform 74 too rapidly if lock assemblies 222 were unlocked when seat section 24 is tilted.

Those skilled in the art will appreciate that many different types of angle sensors, such as mercury switches, potentiometers, rotary encoders, gravity-sensitive resistive devices, and the like may be employed in the control system of deck-positioning assembly 216 to sense the angle of seat section 24 and to disable or enable, as the case may be, actuator 220. Those skilled in the art will also appreciate that angle sensor 298 may be coupled to any one of frame members 34 of seat section 24, panel 44 of seat section 24, or platform 274 and still provide an output signal indicative of the angle of seat section 24. In addition, those skilled in the art will appreciate that it is within the scope of the invention as presently perceived for the output signal from angle sensor 298 to be coupled to additional circuitry that conditions and/or processes the output signal before enabling or disabling actuator 220.

Figure 12:
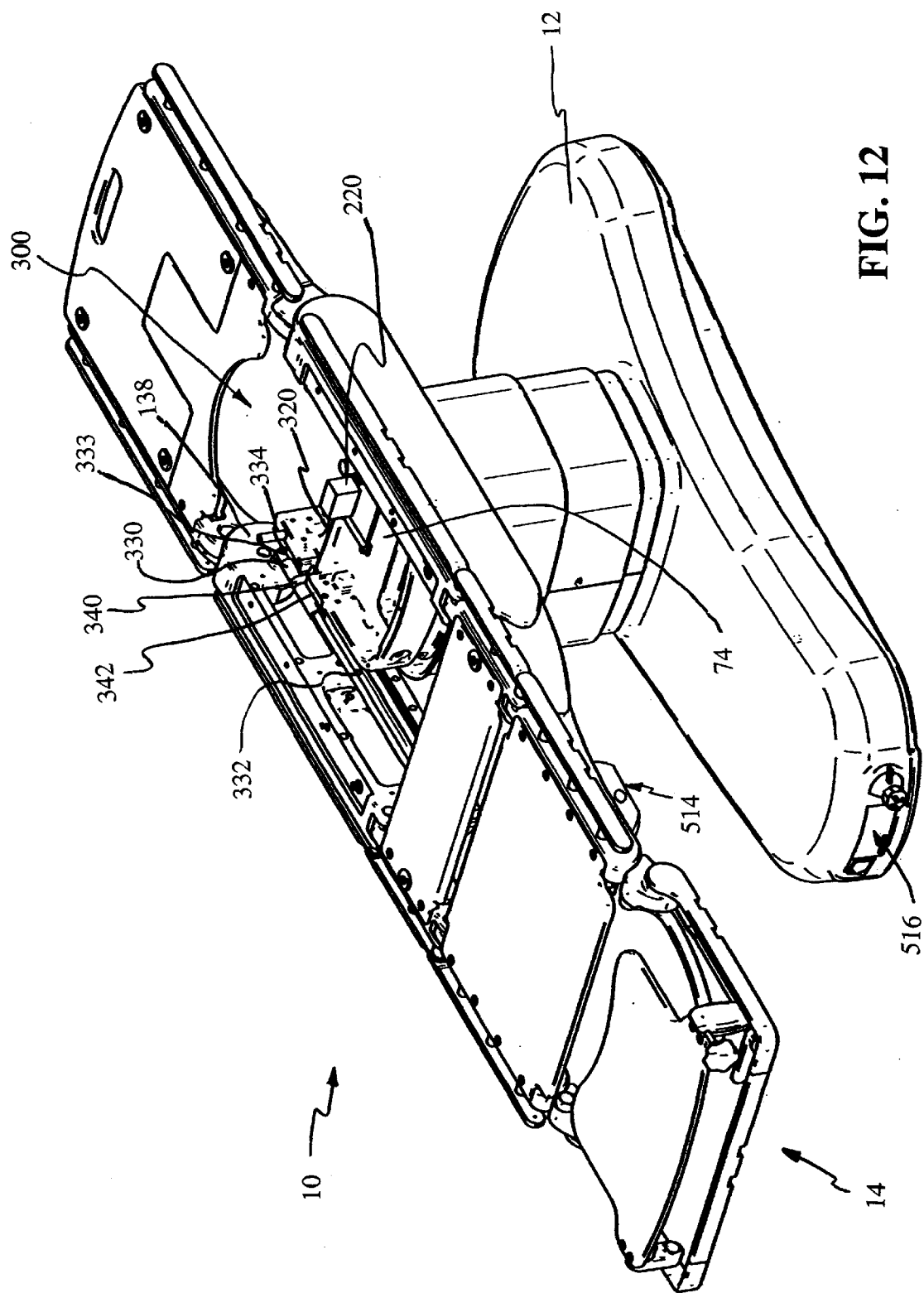
FIG. 12 is a perspective view of another embodiment of a patient-support apparatus of FIG. 1, with portions broken away and detail limited to another embodiment of a locking mechanism, showing the actuator coupled to a locking device by a coupler, a rod coupled to a vertical wall, an a locking device engaging the rod.
Figure 13:
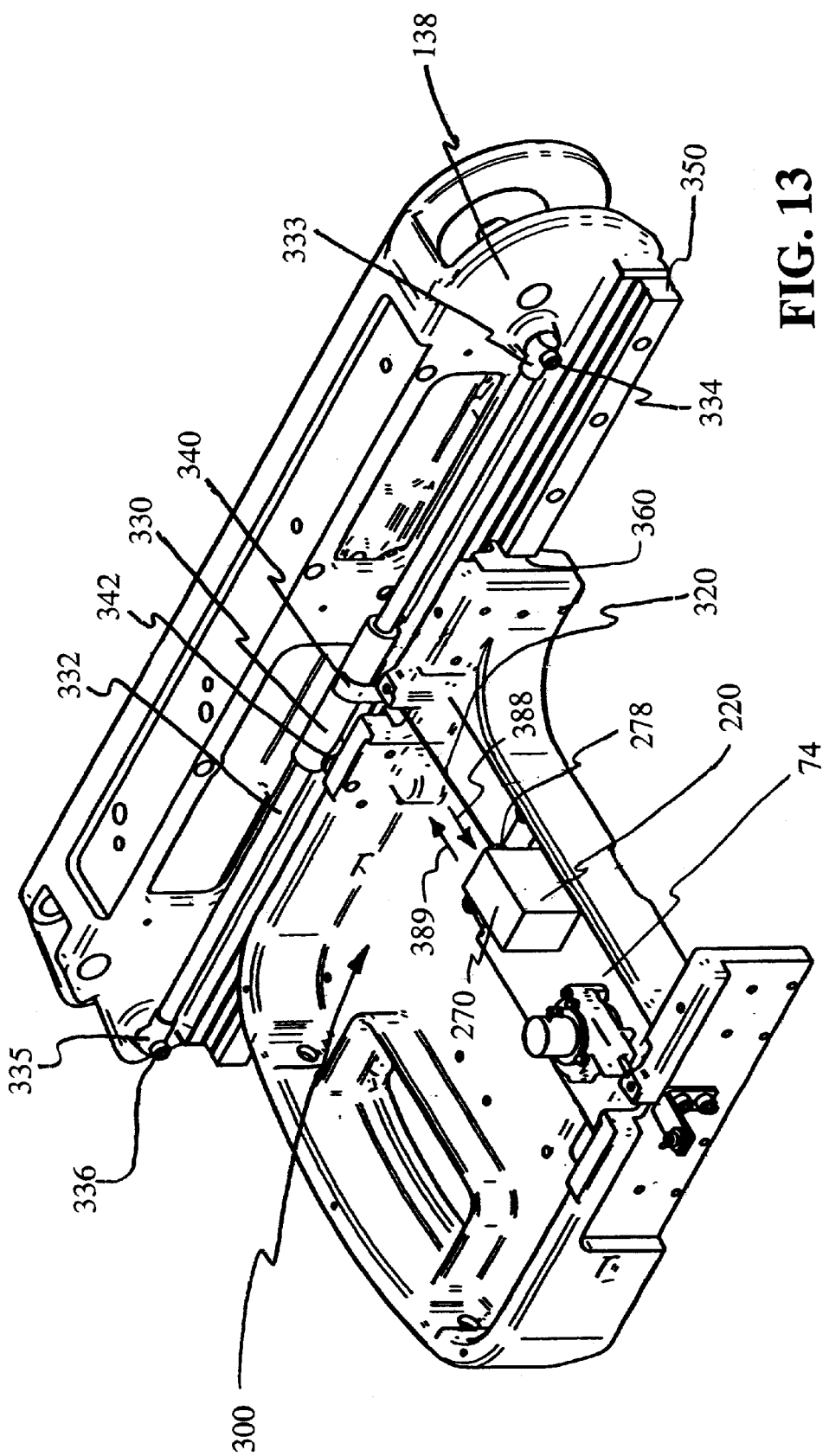
FIG. 13 is another perspective view of the embodiment shown in FIG. 12, showing a slide member of the vertical wall slidably engaging a channel in the platform.
Figure 14:
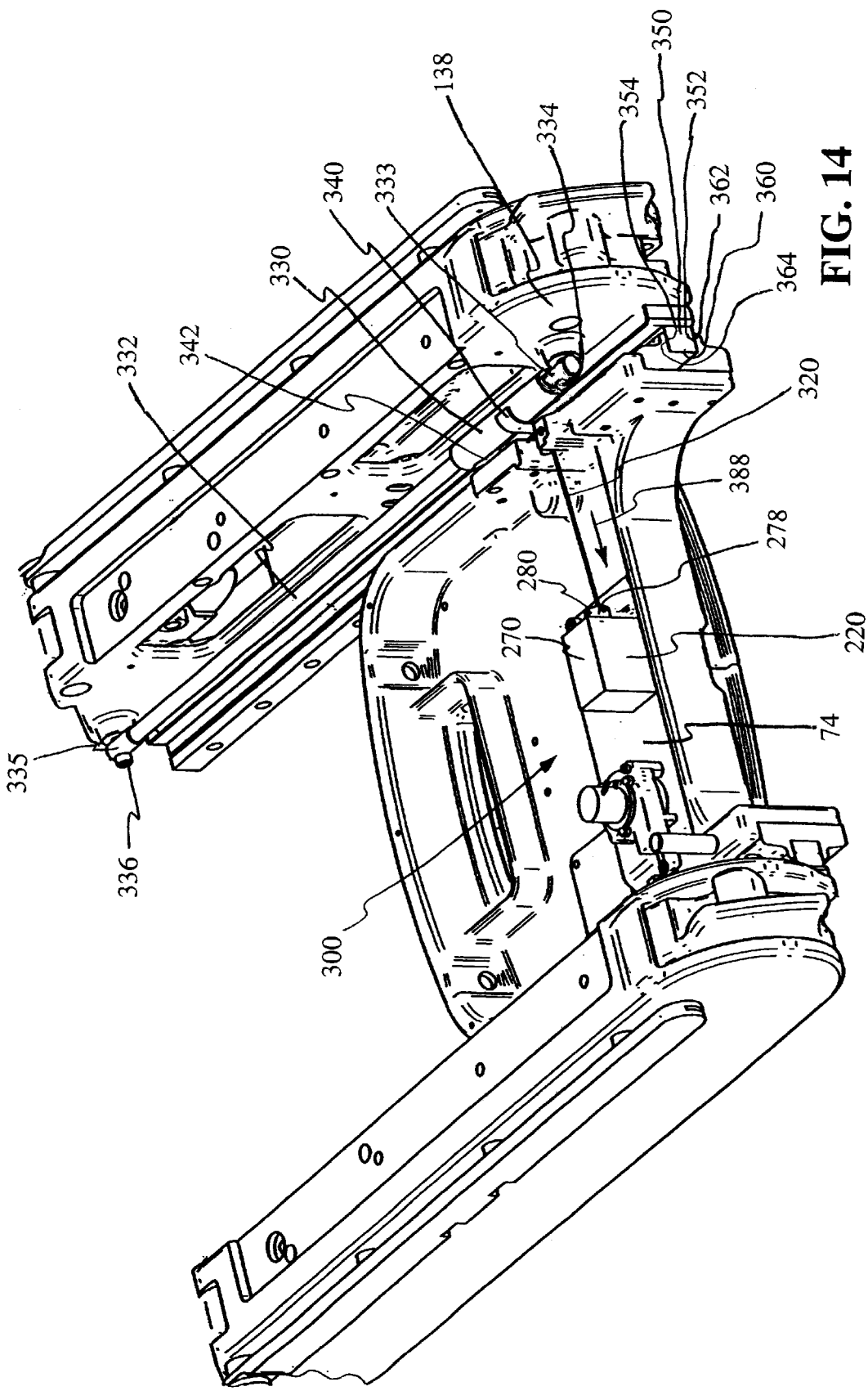
FIG. 14 is another perspective view of the embodiment shown in FIGS. 12 and 13.

Yet another embodiment includes a locking mechanism 300 as described with reference to FIGS. 12–18. FIGS. 12–14 are limited in detail to the embodiment of the locking mechanism 300 described hereafter. However, one skilled in the art will understand that the embodiment of the locking mechanism 300 described hereafter is used in conjunction with the deck-slide mechanism 52 described above.

Referring to FIG. 12, locking mechanism 300 operates to lock and unlock patient-support deck 14 to facilitate longitudinal movement of the deck 14 relative to base 12. Locking mechanism 300 includes a locking device 330 coupled to a rod 332. Locking device 330 engages rod 332 in a first state such that locking device 330 cannot move along the longitudinal axis of rod 332, and disengages rod 332 in a second state such that locking device 330 slides freely along the longitudinal axis of rod 332. Locking device 330 is affixed to platform 74 by clamp 342 or other suitable fastener. Rod 332 is coupled to vertical wall 138 at a first end 333 by bolt 334 and at the second end 335 by bolt 336. Vertical wall 138 includes a slide member 350 having a bottom surface 352 and top surface 354. Slide member 350 is slidably engaged into channel 360 having a bottom surface 362 and top surface 364. Thus, slide member 350 of vertical wall 138 and channel 360 of platform 74 allows vertical wall 138 to slide freely in a longitudinal direction relative to platform 74.

When locking device 330 engages the rod 332 in the first state, longitudinal movement of the patient-support deck 14 relative to the base 12 is prevented, as engagement of locking device 330 to rod 332 prevents longitudinal movement of vertical wall 138 relative to platform 74. Similarly, when locking device 330 disengages the rod 332 in the second state, base 12 can move longitudinally relative patient-support deck 14, as vertical wall 138 can slide freely in a longitudinal direction relative to platform 74.

Switch 340 selects between the first and second state of locking device 330. In the preferred embodiment, locking device 330 is a mechanical linear locking device. One such mechanical linear locking device is manufactured by the P. L. Porter Co. of Woodland Hills, Calif., under the mark MECHLOK®, Model Nos. MM 65, MM 85 and others.

Switch 340 of locking device 330 is coupled to the output shaft 278 of solenoid 220 by coupler 320. Actuation of solenoid 220 places locking device 330 in the second state so that the rod 332 slides freely relative to the locking device 330 along the longitudinal axis of rod 332. Thus, longitudinal movement of patient-support deck 14 relative to base 12 is enabled by actuation of solenoid 220. In the preferred embodiment, coupler 320 is metal rod connected at a first end to switch 340 and at the second end to shaft 278. Coupler 320 can also be realized by a cable or wire linkage coupling switch 340 to shaft 278. When solenoid 220 is actuated in a conventional manner by applying an electric potential to leads (not shown) of solenoid 220, shaft 278 moves in the direction of arrow 388, shown in FIG. 13, such that shaft 278 retracts further into housing 270. As shaft 278 retracts further into housing 270, coupler 320 activates switch 340 of locking device 320, such that locking device 320 disengages rod 332 in the second state and rod 332 slides freely relative to the locking device 330 along the longitudinal axis of rod 332.

After the patient-support deck 14 has been longitudinally moved to a desired position, the solenoid 220 is deactuated by removing the electric potential to leads (not shown) of solenoid 220. Spring 280 forces retraction of shaft 278 from housing 270 in the direction of arrow 389, and coupler 320 deactivates switch 340 such that locking device 330 engages rod 332 in a first state and longitudinal movement of rod 332 relative to locking device 330 is thereby prevented. Accordingly, patient-support deck 14 is prevented from moving in a longitudinal direction relative to base 12.

Solenoid 220 is activated in conjunction with deck-slide mechanism 52 so that locking device 330 disengages rod 332 when deck-slide mechanism 52 is actuated. Patient-support apparatus 210 includes a control system that is used to command the operation of the various drive mechanisms (not shown) of deck-positioning assembly 52 and that is used to command the operation of solenoid or actuator 220. An illustrative portion 394 of the control system associated with actuator 220 of locking mechanism 300 is shown diagrammatically in FIG. 15. User input 296 receives user input commands to lock and unlock locking mechanism 300 thereby controlling locking and unlocking of deck 14 relative to base 12. Controller 410 receives user input 296 and input from angle sensor 298. When input from user input 296 indicates that a user desires to move the patient-support deck 14 in a longitudinal direction relative to base 12, controller 410 checks the output of angle sensor 298. Angle sensor 298 is configured to sense whether seat section 24 is tilted about transverse axis 56. If seat section 24 is tilted in either direction about axis 56, controller 410 will not enable actuator 220. If seat section 24 is in a horizontal position, controller 410 will enable actuator 220. Disabling actuator 220 when seat section 24 is tilted about axis 56 reduces the likelihood that patient-support surface 14 would slide relative to platform 74 too rapidly if locking device 330 were unlocked when seat section 24 is tilted. In the preferred embodiment, controller 410 will not enable actuator 220 if the angle sensor 298 indicates a tilt angle of 3 degrees or greater relative to horizontal.

Those skilled in the art will appreciate that many different types of angle sensors, such as mercury switches, potentiometers, rotary encoders, gravity-sensitive resistive devices, optical angle sensors and the like may be employed in the control system locking mechanism 300 to sense the angle of seat section 24 and to provide a signal to controller 410 to disable or enable, as the case may be, actuator 220. Those skilled in the art will also appreciate that angle sensor 298 may be coupled to any one of frame members 34 of seat section 24, panel 44 of seat section 24, or platform 74 and still provide an output signal indicative of the angle of seat section 24.

Solenoid 220 can either be a continuous duty solenoid or an intermittent duty solenoid. In the preferred embodiment, solenoid 220 is an intermittent duty solenoid. Accordingly, continuous use of solenoid 220 will cause solenoid to overheat and become damaged. Therefore, the activation signal to solenoid 220 is pulse-width-modulated (PWM) to prevent damage to solenoid 220.

Figure 17:
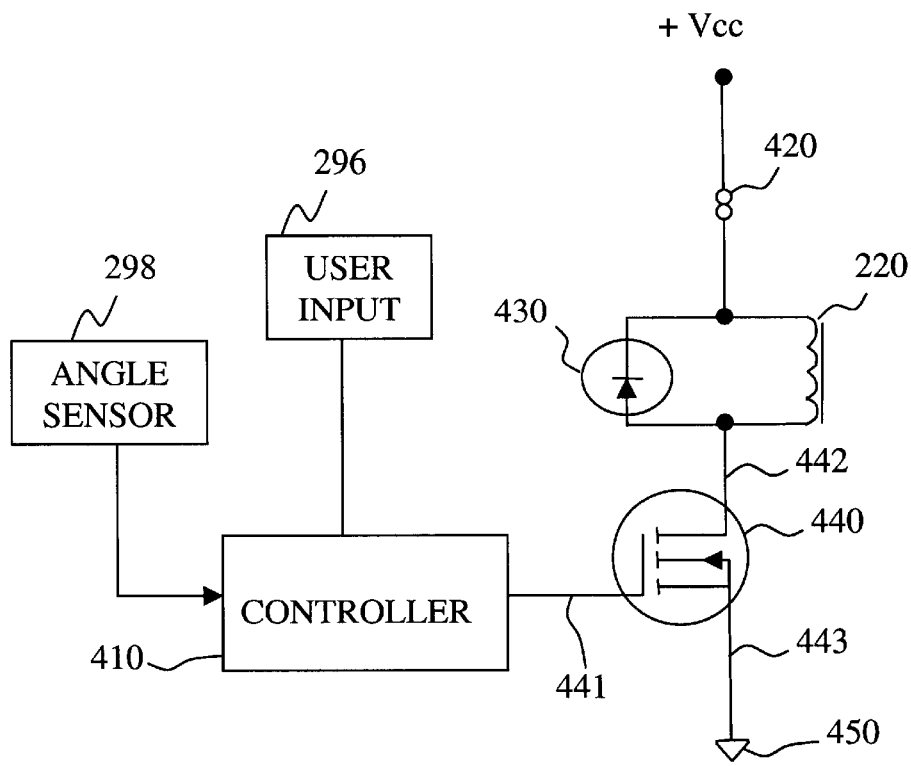
FIG. 17 is a circuit diagram of a portion of a control system for controlling the locking mechanism is FIG. 12, showing a user input, a controller, an N-channel MOSFET, a diode in parallel with the solenoid, a thermal cutoff switch, and a voltage supply.
Figure 18:
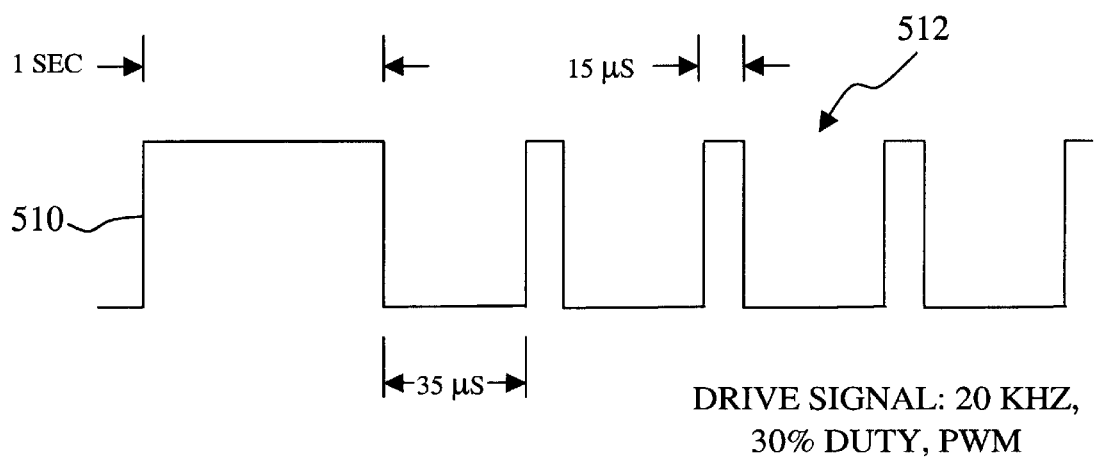
FIG. 18 is a timing diagram illustrating a pulse-width-modulated (PWM) drive signal applied to the MOSFET gate in FIG. 17.

PWM of the activation signal to solenoid 220 is accomplished by the circuit described in FIG. 17. When controller 410 determines from the user input 298 and angle sensor 298 that solenoid 220 is to be actuated, controller 410 provides a drive signal as shown in FIG. 18 to gate 441 of N-channel MOSFET 440. Drive signal comprises a first pulse 510 followed by a pulse train 512. In the preferred embodiment, the first pulse 510 is a 1 second duration pulse, and the pulse train 512 is a 20 KHz, 30% duty cycle signal comprising a 15 μs pulse followed by a 35 μs low signal. N-channel MOSFET 440 acts as switch when the drive signal is applied to gate 441, creating a low resistance path from the drain 442 to source 443 when the drive signal is high (i.e., a "closed" position), and creating an open circuit between drain 442 and source 443 when the drive signal is low (i.e., an "open" position). One of ordinary skill in the art will appreciate that other suitable gate devices, such as a bipolar junction transistor (BJT), can be used to implement the switching function of N-channel MOSFET 440.

When the N-channel MOSFET 440 is conducting between the drain 442 and source 443, Voltage source $V_{cc}$ actuates solenoid 220. As more power is required to pull shaft 278 inward toward housing 270 as is required to hold shaft 278 in housing 270 after the solenoid 220 is activated, the 1 second pulse 510 is applied before the pulse train 512. After the initial pulse 510, pulse train 510 is applied to gate 441. As conduction between drain 442 and source 443 is prevented when a low signal is applied to gate 441, flyback diode 430 provides an alternate current path through which the current in solenoid 220 coil dissipates. Thermal cutoff switch 420 ensures that solenoid 220 is not damaged by cutting out voltage source $V_{cc}$ if solenoid 220 experiences a temperature above its normal rating.

Figure 16:
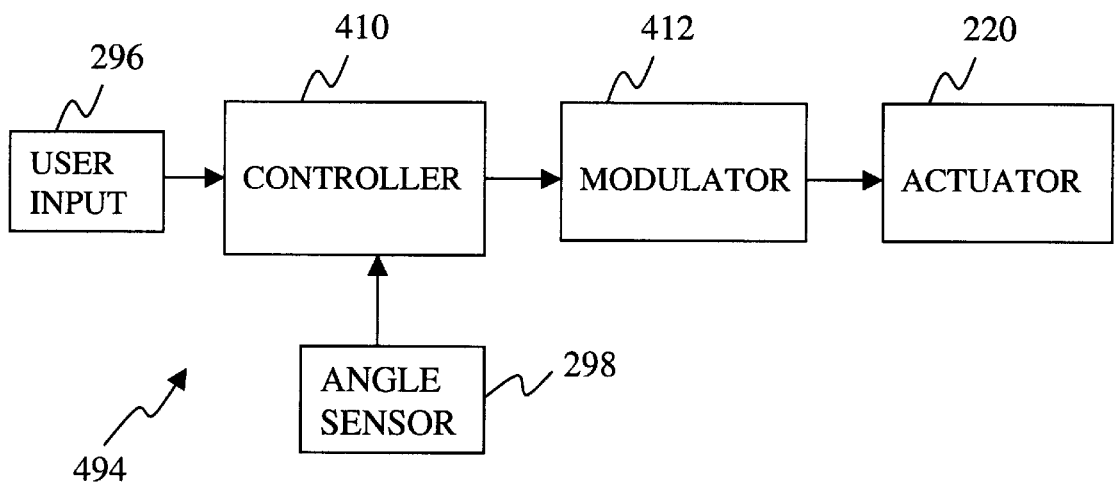
FIG. 16 is a block diagram of a portion of a control system for controlling the locking mechanism of FIG. 12, showing a user input block, an angle sensor block, a controller block, a modulator block, and an actuator block.

Controller 410 is programmed to provide the drive signal of FIG. 18, and thus the PWM signal is can be adjusted to suit solenoids of varying parameters. Of course, one of ordinary skill will appreciate an alternative embodiment in which controller provides an activation signal to a separate modulator 412, as shown in FIG. 16. Modulator 412 outputs a drive signal as shown in FIG. 18 as long as modulator 412 receives an activation signal from controller 410. Illustratively, modulator 412 is realized by coupling the outputs of a one-shot multivibrator configured to provide a 1 second pulse and an oscillator configured to provide a 20 KHz, 30% duty cycle pulse train to an OR gate. Likewise, one of ordinary skill will appreciate that a discrete logic circuit can be substituted to provide the same functionality of controller 410.

Locking mechanism 300 as disclosed herein provides infinite positioning over the longitudinal range of rod 332 and is also used in conjunction with a manual slide mechanism for enabling longitudinal movement of a patient-support deck 14 relative to base 12. Illustratively, a manual slide mechanism is realized by eliminating the powered drive system as described with reference to FIGS. 1–7 above. In a manual slide patient-support surface, a user input, such as a button, squeeze grip, or a foot pedal, is provided. Locking mechanism 300 is normally in the first state (i.e., a locked state) to prevent longitudinal movement of patient-support deck 14 relative to base 12. A user activates the user input and locking mechanism 300 is placed in the second state (i.e., an unlocked state) so that the user may manually move patient-support deck 14 in a longitudinal direction relative to base 12.

Figure 15:
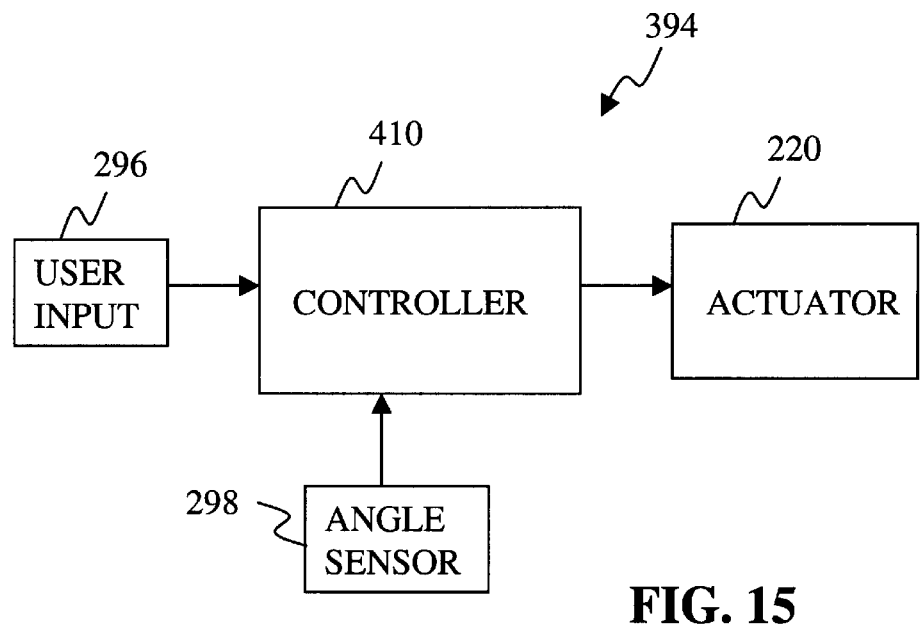
FIG. 15 is a block diagram of a portion of a control system for controlling the locking mechanism of FIG. 12, showing a user input block, an angle sensor block, a controller block, and an actuator block.

The same control device of FIG. 15 is used in the manual slide patient-support surface as previously described. Activation of the user input provides the corresponding user input signal to controller 410. Thus, user input 296 receives user input commands to lock and unlock locking mechanism 300 thereby controlling locking and unlocking of deck 14 relative to base 12. Controller 410 receives user input 296 and input from angle sensor 298. When input from user input 296 indicates that a user desires to move the patient-support deck 14 in a longitudinal direction relative to base 12, controller 410 checks the output of angle sensor 298. Angle sensor 298 is configured to sense whether seat section 24 is tilted about transverse axis 56. If seat section 24 is tilted in either direction about axis 56, controller 410 will not enable actuator 220. If seat section 24 is in a horizontal position, controller 410 will enable actuator 220. Disabling actuator 220 when seat section 24 is tilted about axis 56 reduces the likelihood that patient-support deck 14 would slide relative to platform 74 too rapidly if locking device 330 were unlocked when seat section 24 is tilted. In the preferred embodiment, controller 410 will not enable actuator 220 if the angle sensor 298 indicates a tilt angle of 3 degrees or greater relative to horizontal.

As discussed above a user input switch 296 is located on a portion of the deck 14 as illustrated, for example, by switch 514 in FIG. 12. Switch 514 is illustratively a membrane switch or other type of conventional switch. User input 296 may also be provided by an auxiliary switch panel 516 on base 12. By locating the switch panel 516 on base 12, the panel is not covered by a drape, is more accessible to an anesthesiologist at a head end of the apparatus 10, and does not interfere with other equipment on deck 14.

Although the invention has been described in detail with reference to certain preferred embodiments, one of ordinary skill in the art will appreciate that the invention is not limited to the preferred embodiments described here. In an alternative embodiment, locking mechanism 300 includes rod 332 coupled to platform 74 and locking device 330 and actuator 220 are coupled to vertical wall 138. Additional variations and modifications exist within the scope and spirit of the invention as described and defined in the following claims.

What is claimed is:

1. A patient-support apparatus, comprising:
   a base;
   a patient-support deck having a longitudinal length and a transverse width;
   a rod coupled to the patient-support deck; and
   a deck-positioning assembly coupling the patient-support deck to the base, the patient-support deck being supported with respect to the deck-positioning assembly for longitudinal movement relative to the base, the deck-positioning assembly including a locking device, the locking device including a portion moveable between first and second positions, the portion of the locking device being configured to engage the rod in the first position to prevent longitudinal movement of the patient-support deck relative to the base, and the portion of the locking device being configured to disengage the rod in the second position to allow longitudinal movement of the patient-support deck relative to the base.

2. The patient-support apparatus of claim 1, wherein the deck-positioning assembly includes an actuator for selecting between the first position and the second position of the locking device.

3. The patient-support apparatus of claim 2, further including a coupling to couple the actuator to the locking device.

4. The patient-support apparatus of claim 3, wherein the actuator is a solenoid.

5. The patient-support apparatus of claim 2, further comprising a controller, the controller configured to receive a user input and provide a drive signal based on the user input, the drive signal actuating the actuator to select the second position of the locking device.

6. The patient-support apparatus of claim 5, further comprising an angle sensor coupled to the deck-positioning assembly and configured to sense a position of at least a portion of the patient-support deck, the angle sensor generating an angle signal when the portion of the patient-support deck is in a tilted position, and wherein the controller is further configured to receive the angle signal from the angle sensor to prevent actuation of the actuator when the portion of the patient-support deck is in the tilted position.

7. The patient-support apparatus of claim 6, wherein the drive signal is a pulse-width-modulated signal.

8. The patient-support apparatus of claim 1, wherein the locking device is a mechanical linear locking device.

9. The patient-support apparatus of claim 8, further comprising a controller, the controller configured to receive a user input and provide a drive signal based on the user input, the drive signal actuating the actuator to select the second position of the locking device.

10. The patient-support apparatus of claim 9, further comprising an angle sensor coupled to the deck-positioning assembly and configured to sense a position of at least a portion of the patient-support deck, the angle sensor generating an angle signal when the portion of the patient-support deck is in a tilted position, and wherein the controller is further configured to receive the angle signal from the angle sensor to prevent actuation of the actuator when the portion of the patient-support deck is in the tilted position.

11. The patient-support apparatus of claim 9, wherein the drive signal is a pulse-width-modulated signal.

12. The patient-support apparatus of claim 2, further comprising a circuit, the circuit configured to receive a user input and provide a drive signal based on the user input, the drive signal actuating the actuator to select the second position of the locking device.

13. The patient-support apparatus of claim 12, wherein the drive signal is a pulse-width-modulated signal.

14. The patient-support apparatus of claim 1, wherein the rod extends parallel to a longitudinal axis of the patient-support deck.

15. A patient-support apparatus, comprising:
    a base;
    a patient-support deck having a longitudinal length and a transverse width;
    a rod coupled to the patient-support deck;
    a deck-positioning assembly coupling the patient-support deck to the base, the patient-support deck being supported with respect to the deck-positioning assembly for longitudinal movement relative to the base, the deck-positioning assembly including a locking device, the locking device configured to engage the rod in a first state to prevent longitudinal movement of the patient-support deck relative to the base, and disengage the rod in a second state to allow longitudinal movement of the patient-support deck relative to the base, wherein the deck-positioning assembly includes an actuator for selecting between the first state and the second state of the locking device; and
    an angle sensor coupled to the deck-positioning assembly and configured to sense a position of at least a portion of the patient-support deck, the angle sensor generating an angle signal that prevents the actuator from selecting the second state of the locking device when the portion of the patient-support deck is in a tilted position.

16. A patient-support apparatus comprising:
    a base;
    a patient-support deck having a longitudinal length and a transverse width;
    a locking device coupled to the patient-support deck;
    a deck-positioning assembly coupling the patient-support deck to the base, the patient-support deck being supported with respect to the deck-positioning assembly for longitudinal movement relative to the base, the deck-positioning assembly including a longitudinal member, and wherein the locking device is configured to engage the longitudinal member to prevent longitudinal movement of the patient-support deck relative to the base; and
    an actuator configured to disengage the locking device from the longitudinal member and thereby allow longitudinal movement of the patient-support deck relative to the base.

17. The patient-support apparatus of claim 16, further comprising a controller, the controller configured to receive a user input and provide a drive signal based on the user input, the drive signal actuating the actuator to disengage the locking device from the longitudinal member.

18. The patient-support apparatus of claim 17, further comprising an angle sensor coupled to the deck-positioning assembly and configured to sense a position of at least a portion of the patient-support deck, the angle sensor generating an angle signal when the portion of the patient-support deck is in a tilted position, and wherein the controller is further configured to receive the angle signal from the angle sensor to selectively prevent actuation of the actuator.

19. The patient-support apparatus of claim 16, wherein the longitudinal member is a rod.

20. The patient-support apparatus of claim 19, wherein the locking device is a mechanical linear locking device.

21. The patient-support apparatus of claim 16, wherein the locking device in a first position is in contact with the longitudinal member in order to prevent longitudinal movement of the patient-support deck relative to the base, and the locking device in a second position is spaced apart from the longitudinal member in order to allow longitudinal movement of the patient-support deck relative to the base.

22. The patient-support apparatus of claim 16, the deck-positioning assembly further including a deck actuator that selectively urges longitudinal movement of the patient-support deck relative to the base.

23. The patient-support apparatus of claim 16, wherein the locking device is mechanically actuated.

24. The patient-support apparatus of claim 16, wherein the locking device includes a portion which moves transversely relative to the patient-support deck from a first position in engagement with the longitudinal member to a second position in spaced relation to the longitudinal member.

25. A patient-support apparatus comprising:
a base;
a patient-support deck having a longitudinal length and a transverse width;
a longitudinal member coupled to the patient-support deck; and
a deck-positioning assembly coupling the patient-support deck to the base, the patient-support deck being supported with respect to the deck-positioning assembly for longitudinal movement relative to the base, the deck-positioning assembly including a locking device, the locking device including a portion having a first position engaging the longitudinal member to prevent longitudinal movement of the patient-support deck relative to the base and having a second position disengaging the longitudinal member and thereby longitudinal movement of the patient-support deck relative to the base.

26. The patient-support apparatus of claim 25, wherein the deck-positioning assembly includes an actuator for selecting between the first position and the second position of the portion of the locking device.

27. The patient-support apparatus of claim 26, further including a coupling to couple the actuator to the locking device.

28. The patient-support apparatus of claim 27, wherein the actuator is a solenoid.

29. The patient-support apparatus of claim 27, further comprising an angle sensor coupled to the deck-positioning assembly and configured to sense a position of at least a portion of the patient-support deck, the angle sensor generating an angle signal that prevents the actuator from selecting the second position of the portion of the locking device when the portion of the patient-support deck is in a tilted position.

30. The patient support apparatus of claim 26, further comprising a controller, the controller configured to receive a user input and provide a drive signal based on the user input, the drive signal actuating the actuator to select the second position of the portion of the locking device.

31. The patient-support apparatus of claim 30, further comprising an angle sensor coupled to the deck-positioning assembly and configured to sense a position of at lease a portion of the patient-support deck, the angle sensor generating an angle signal when the portion of the patient-support deck is in a tilted position, and wherein the controller is further configured to receive the angle signal from an angle sensor to prevent actuation of the actuator when the portion of the patient-support deck is in the tilted position.

32. The patient-support apparatus of claim 25, wherein the locking device is a mechanical linear locking device.

33. The patient-support apparatus of claim 32, further comprising a controller, the controller configured to receive a user input and provide a drive signal based on the user input, the drive signal causing the portion of the locking device to move to the second position.

34. The patient-support apparatus of claim 33, further comprising an angle sensor coupled to the deck-positioning assembly and configured to sense a position of at least a portion of the patient-support deck, the angle sensor generating an angle signal when the portion of the patient-support deck is in a tilted position, and wherein the controller is further configured to receive the angle signal from the angle sensor to prevent movement of the portion of the locking device when the portion of the patient-support deck is in the tilted position.

35. The patient-support apparatus of claim 26, further comprising a circuit, the circuit configured to receive a user input and provide a drive signal based on the user input, the drive signal actuating the actuator to select the second state of the locking device.

36. A patient-support apparatus, comprising:
a base;
a patient-support deck having a longitudinal length and a transverse width, the patient-support deck being supported with respect to the deck-positioning assembly for longitudinal movement relative to the base;
a locking device operably coupled to the patient-support deck and configured to prevent longitudinal movement of the patient-support deck relative to the base in a locked state and to allow longitudinal movement of the patient-support deck relative to the base in an unlocked state;
an actuator operably coupled to the locking device and configured to select between the locked state and the unlocked state of the locking device;
a controller operably coupled to the actuator and configured to provide a drive signal to the actuator;
an angle sensor operably coupled to the patient-support deck, the angle sensor configured to sense an angular position of at least a portion of the patient-support deck relative to a transverse axis, the angle sensor further configured to generate an angle signal indicative of the angular position of the portion of the patient-support deck; and
wherein the controller is configured to receive the angle signal from the angle sensor, and to prevent the actuator from placing the locking device in the unlocked state when the patient-support deck is tilted by at least a predetermined angle from horizontal.

37. The patient-support apparatus of claim 36, further comprising a longitudinal member coupled to the patient-support deck, the locking device being configured to engage the longitudinal member in the locked state and to disengage the longitudinal member in the unlocked state.

38. The patient-support apparatus of claim 36, wherein the actuator is a solenoid.

39. The patient-support apparatus of claim 36, wherein the controller is further configured to receive a user input and generate the drive signal in response to the user input, the drive signal actuating the actuator to select the unlocked state of the locking device.

40. The patient-support apparatus of claim 36, wherein the predetermined angle is approximately zero degrees from horizontal.

* * * * *